(12) United States Patent
Rioux

(10) Patent No.: US 11,534,145 B2
(45) Date of Patent: Dec. 27, 2022

(54) BONE MARROW ACCESS APPARATUS AND METHODS FOR LOCATING SAME

(71) Applicant: APERTURE MEDICAL TECHNOLOGY LLC, New York, NY (US)

(72) Inventor: Bob Rioux, Ashland, MA (US)

(73) Assignee: APERTURE MEDICAL TECHNOLOGY LLC, New York, NY (US)

( * ) Notice: Subject to any disclaimer, the term of this patent is extended or adjusted under 35 U.S.C. 154(b) by 996 days.

(21) Appl. No.: 16/158,568

(22) Filed: Oct. 12, 2018

(65) Prior Publication Data
US 2020/0113552 A1 Apr. 16, 2020

(51) Int. Cl.
| | |
|---|---|
| A61B 10/02 | (2006.01) |
| A61B 17/34 | (2006.01) |
| A61B 17/16 | (2006.01) |
| A61M 39/02 | (2006.01) |
| A61B 17/00 | (2006.01) |

(52) U.S. Cl.
CPC ........ *A61B 10/025* (2013.01); *A61B 17/1615* (2013.01); *A61B 17/3423* (2013.01); *A61M 39/0247* (2013.01); *A61B 17/3472* (2013.01); *A61B 17/3498* (2013.01); *A61B 2010/0258* (2013.01); *A61B 2017/00685* (2013.01); *A61B 2017/3419* (2013.01);
(Continued)

(58) Field of Classification Search
CPC .......................... A61B 10/025; A61B 17/1615
See application file for complete search history.

(56) References Cited

U.S. PATENT DOCUMENTS 2,219,605 A * 10/1940 Turkel ................. A61B 10/025
604/164.01
2,919,692 A 1/1960 Wolfgang
(Continued)

FOREIGN PATENT DOCUMENTS

| CN | 104414714 A | 3/2015 |
|---|---|---|
| GB | 1324759 A | 7/1973 |

(Continued)

OTHER PUBLICATIONS

Japanese Office Action (and English language translation thereof) dated Jan. 19, 2022, issued in Japanese Application No. 2021-025913.
(Continued)

*Primary Examiner* — Christian A Sevilla
(74) *Attorney, Agent, or Firm* — Holtz, Holtz & Volek PC

(57) ABSTRACT

Bone marrow access apparatus includes a bone penetrating member and a cap. The bone penetrating member includes a tubular insertion portion, and a head portion provided at a proximal end of the tubular insertion portion. A cross-sectional shape of the head portion is wider than a cross-sectional shape of the tubular insertion portion. A recess is provided in the head portion, and an internal channel is provided through the head portion and the tubular insertion portion. The cap accommodates the head portion of the bone penetrating member therein. The cap includes a lower wall which covers at least a part of a distal side of the head portion, and a projection which projects into the recess of the head portion.

18 Claims, 54 Drawing Sheets

(52) U.S. Cl.
CPC .......... *A61M 2039/0202* (2013.01); *A61M 2039/025* (2013.01); *A61M 2202/10* (2013.01)

(56) References Cited

U.S. PATENT DOCUMENTS

| | | | |
|---|---|---|---|
| 4,142,517 A | 3/1979 | Contreras Guerrero de Stavropoulos et al. | |
| 4,403,617 A | 9/1983 | Trelinyak | |
| 4,519,514 A | 5/1985 | Agbay et al. | |
| 4,738,261 A | 4/1988 | Enstrom | |
| 4,772,261 A | 9/1988 | Von Hoff et al. | |
| 5,104,389 A | 4/1992 | Deem et al. | |
| 5,122,114 A * | 6/1992 | Miller ............ | A61M 39/0208 604/48 |
| 5,273,545 A | 12/1993 | Hunt et al. | |
| 5,332,398 A | 7/1994 | Miller et al. | |
| 5,372,583 A | 12/1994 | Roberts et al. | |
| 5,405,388 A | 4/1995 | Fox | |
| 5,451,210 A | 9/1995 | Kramer et al. | |
| 5,456,267 A | 10/1995 | Stark | |
| 5,601,559 A | 2/1997 | Melker et al. | |
| 5,720,753 A * | 2/1998 | Sander ............ | A61F 2/0811 606/104 |
| 5,727,770 A | 3/1998 | Dennis | |
| 5,743,861 A | 4/1998 | Columbus et al. | |
| 5,817,062 A | 10/1998 | Flom et al. | |
| 5,990,382 A | 11/1999 | Fox | |
| 6,018,094 A | 1/2000 | Fox | |
| 6,033,369 A | 3/2000 | Goldenberg | |
| 6,165,168 A | 12/2000 | Russo | |
| 7,670,328 B2 | 3/2010 | Miller | |
| 7,833,204 B2 | 11/2010 | Picha | |
| 7,951,089 B2 | 5/2011 | Miller | |
| 8,079,979 B2 | 12/2011 | Moorehead | |
| 8,142,365 B2 | 3/2012 | Miller | |
| 8,372,061 B2 | 2/2013 | Berna et al. | |
| 8,419,683 B2 | 4/2013 | Miller | |
| 8,500,819 B2 | 8/2013 | Meridew | |
| 8,690,791 B2 | 4/2014 | Miller | |
| 8,715,287 B2 | 5/2014 | Miller | |
| 8,801,670 B2 | 8/2014 | Drontle et al. | |
| 8,852,119 B2 | 10/2014 | Wawrzyniak | |
| 8,870,872 B2 | 10/2014 | Miller | |
| 8,876,826 B2 | 11/2014 | Miller | |
| 8,992,442 B2 | 3/2015 | Cortes Ramirez et al. | |
| 8,992,535 B2 | 3/2015 | Miller | |
| 8,998,848 B2 | 4/2015 | Miller et al. | |
| 9,072,543 B2 | 7/2015 | Miller et al. | |
| 9,078,637 B2 | 7/2015 | Miller | |
| 9,125,639 B2 | 9/2015 | Mathis | |
| 9,301,736 B2 | 4/2016 | Rusnak | |
| 9,314,228 B2 | 4/2016 | Miller | |
| 9,433,400 B2 | 9/2016 | Miller | |
| 9,451,968 B2 | 9/2016 | Miller et al. | |
| 9,770,425 B2 | 9/2017 | Solomon | |
| 10,426,940 B2 * | 10/2019 | Aklog ............ | A61M 39/02 |
| 10,448,933 B2 | 10/2019 | Rioux et al. | |
| 10,517,576 B2 | 12/2019 | Rioux et al. | |
| 2002/0082519 A1 | 6/2002 | Miller et al. | |
| 2003/0032922 A1 | 2/2003 | Moorehead | |
| 2003/0093034 A1 | 5/2003 | Chang et al. | |
| 2003/0225344 A1 | 12/2003 | Miller | |
| 2004/0127905 A1 | 7/2004 | Lim | |
| 2004/0215102 A1 | 10/2004 | Ikehara et al. | |
| 2005/0148940 A1 | 7/2005 | Miller | |
| 2006/0167378 A1 | 7/2006 | Miller | |
| 2006/0167379 A1 | 7/2006 | Miller | |
| 2006/0167416 A1 | 7/2006 | Mathis et al. | |
| 2006/0247552 A1 | 11/2006 | Ikehara et al. | |
| 2007/0088277 A1 | 4/2007 | Mcginley et al. | |
| 2007/0197935 A1 | 8/2007 | Reiley et al. | |
| 2007/0270712 A1 | 11/2007 | Wiksell et al. | |
| 2007/0270775 A1 | 11/2007 | Miller et al. | |
| 2008/0015467 A1 | 1/2008 | Miller | |
| 2008/0015468 A1 | 1/2008 | Miller | |
| 2008/0065083 A1 | 3/2008 | Truckai et al. | |
| 2008/0215056 A1 | 9/2008 | Miller et al. | |
| 2008/0287910 A1 | 11/2008 | Picha | |
| 2009/0054808 A1 | 2/2009 | Miller | |
| 2010/0137740 A1 | 6/2010 | Miller | |
| 2010/0234761 A1 | 9/2010 | Cortes et al. | |
| 2010/0298784 A1 | 11/2010 | Miller | |
| 2011/0076640 A1 | 3/2011 | Jones | |
| 2011/0137352 A1 | 6/2011 | Biedermann et al. | |
| 2011/0218644 A1 | 9/2011 | Meridew et al. | |
| 2012/0095440 A1 * | 4/2012 | Islam ............ | A61M 39/0208 604/506 |
| 2012/0116247 A1 | 5/2012 | Wawrzyniak et al. | |
| 2013/0190817 A1 | 7/2013 | Bouduban et al. | |
| 2013/0304116 A1 | 11/2013 | Yamane | |
| 2014/0018699 A1 | 1/2014 | Rusnak | |
| 2014/0150782 A1 | 6/2014 | Vazales | |
| 2014/0207084 A1 | 7/2014 | Webb et al. | |
| 2014/0288499 A1 | 9/2014 | Miller | |
| 2015/0314118 A1 | 11/2015 | Kelekis | |
| 2016/0015893 A1 | 1/2016 | Hoyt et al. | |
| 2016/0136410 A1 | 5/2016 | Aklog et al. | |
| 2016/0331401 A1 | 11/2016 | Dreyfuss et al. | |
| 2017/0216564 A1 | 8/2017 | Devgon et al. | |
| 2018/0092632 A1 | 4/2018 | Rioux et al. | |
| 2018/0092662 A1 | 4/2018 | Rioux et al. | |
| 2018/0093094 A1 | 4/2018 | Wolf | |
| 2018/0256869 A1 | 9/2018 | Aklog et al. | |
| 2019/0388066 A1 | 12/2019 | Rioux et al. | |
| 2019/0388067 A1 | 12/2019 | Rioux et al. | |

FOREIGN PATENT DOCUMENTS

| | | |
|---|---|---|
| GB | 2289415 A | 11/1995 |
| JP | S535654 U | 1/1978 |
| JP | H03111025 A | 5/1991 |
| JP | 2001104323 A | 4/2001 |
| JP | 2003116862 A | 4/2003 |
| JP | 2013233283 A | 11/2013 |
| WO | 2014070804 A1 | 5/2014 |
| WO | 2016057090 A1 | 4/2016 |
| WO | 2018067525 A1 | 4/2018 |

OTHER PUBLICATIONS

Partial Supplementary European Search Report dated Jan. 31, 2022, issued in counterpart European Application No. 19871573.2.
Extended European Search Report (EESR) dated Jun. 2, 2021 issued in European Application No. 21157097.3.
Extended European Search Report (EESR) dated Apr. 23, 2020 issued in European Patent Application No. 17858996.6.
Notice of Allowance dated Jul. 27, 2021 issued in related U.S. Appl. No. 16/559,811.
International Search Report and Written Opinion for PCT/US2015/036407 dated Sep. 30, 2015.
International Search Report for PCT/US2017/054883 dated Jan. 18, 2018.
Written Opinion for PCT/US2017/054883 dated Jan. 18, 2018.
Abstract of CN 104414714A.
Anwarul Islam, Induction treatment of acute myeloid leukemia in an elderly patient with intramarrow injection/administration of cytarabine: first report of a case, Clinical Case Reports 2015; 3(12): 1026-1029.
Valerie A. Rosetti et al., Intraosseous Infusion: An Alternative Route of Pediatric Intravascular Access, Annals of Emergency Medicine, 14:9 Sep. 1985.
Office Action (Non-Final Rejection) dated Aug. 27, 2021 issued in related U.S. Appl. No. 16/559,870.
Japanese Office Action (and English language translation thereof) dated Jul. 22, 2020 issued in Japanese Application No. 2019-518968.
Interational Search Report (ISR) and Written Opinion dated Feb. 5, 2020 issued in International Application No. PCT/US2019/053920.
Japanese Office Action (and English language translation thereof) dated Jun. 15, 2022, issued in counterpart Japanese Application No. 2021-519727.

(56) References Cited

OTHER PUBLICATIONS

Japanese Office Action (and English language translation thereof) dated Sep. 7, 2022, issued in Japanese Application No. 2021-025913.

* cited by examiner

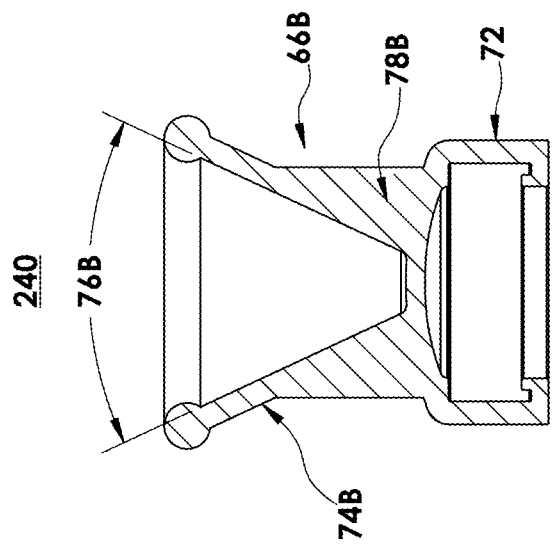
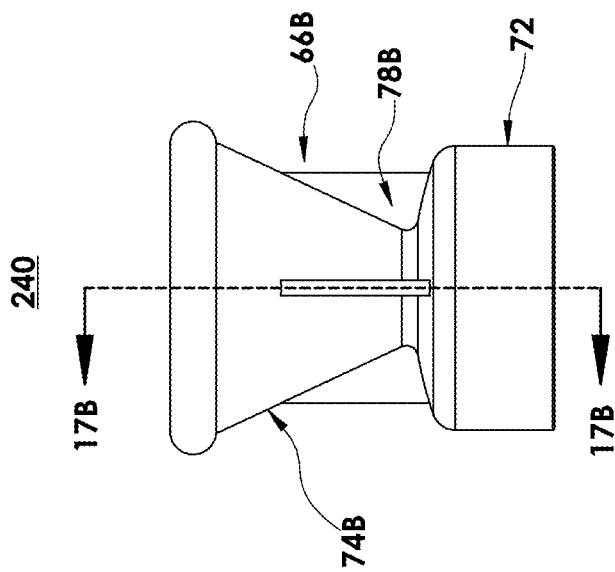

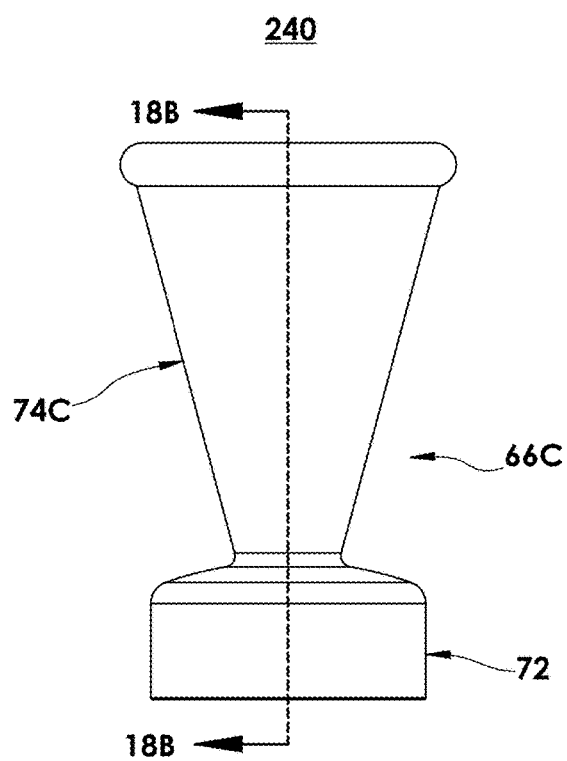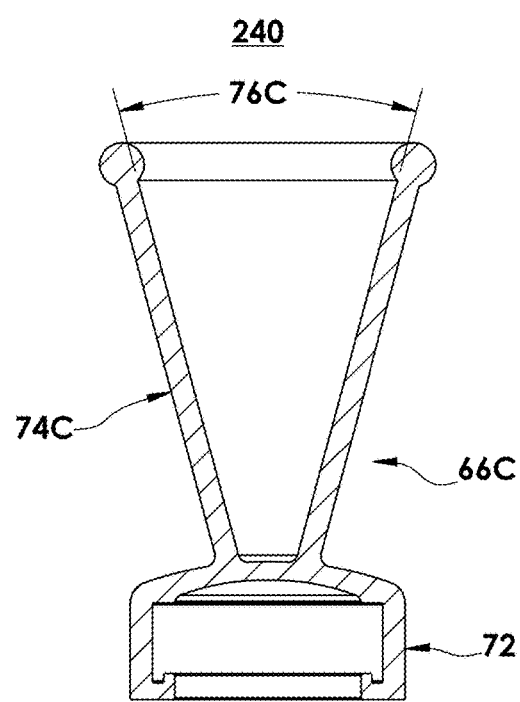
Fig. 18A
Fig. 18B

BONE MARROW ACCESS APPARATUS AND METHODS FOR LOCATING SAME

FIELD OF THE INVENTION

The present invention relates generally to a bone marrow access apparatus capable of providing repeatable access to a patient's bone marrow, methods for installing a bone marrow access apparatus, and tools and methods for locating a bone marrow access apparatus when installed.

BACKGROUND OF THE INVENTION

Bone marrow is the major site of blood cell formation and, while at birth it is found within nearly all bones, by adolescence it is located primarily within axial bones (e.g., pelvis and femur). The bone marrow exists in the inner portion of bones, referred to herein as the marrow space, and contains the precursor stem cells that ultimately become red blood cells, white blood cells, and platelets.

Bone marrow aspirations and biopsies are common tests used to evaluate the bone marrow for leukemias and other hematologic disorders, for example. A sampling of the marrow from the marrow space can determine cell number, cell shape, and cell maturation. Special pathologic stains and molecular studies on the marrow specimens can establish certain diagnoses. Sampling of marrow from the marrow space may occur at multiple times during a patient's treatment program to assess progress.

Conventionally, in order to access bone marrow of a patient, the bone is punctured each time a doctor needs to access the marrow. This is painful for the patient, and imposes a significant burden on the doctor and healthcare resources. There exists a need for an implantable bone marrow access apparatus that can be retained subcutaneously in the bone of a patient throughout the course of treatment to allow repeated access to the bone marrow without requiring repeated bone punctures.

SUMMARY OF THE INVENTION

According to one embodiment, a bone marrow access apparatus includes a bone penetrating member and a cap. The bone penetrating member includes a tubular insertion portion, and a head portion provided at a proximal end of the tubular insertion portion, a cross-sectional shape of the head portion being wider than a cross-sectional shape of the tubular insertion portion. A recess is provided in the head portion, and an internal channel is provided through the head portion and the tubular insertion portion. The cap accommodates the head portion of the bone penetrating member therein. The cap includes a lower wall which covers at least a part of a distal side of the head portion, and a projection which projects into the recess of the head portion.

According to another embodiment, a bone marrow access apparatus includes a bone penetrating member, and a tactile feedback member which is coupled to the bone penetrating member. The bone penetrating member includes a tubular insertion portion, and a head portion provided at a proximal end of the tubular insertion portion, a cross-sectional shape of the head portion being wider than a cross-sectional shape of the tubular insertion portion, and an internal channel provided through the head portion and the tubular insertion portion. The tactile feedback member is provided at a distal side of the head portion of the bone penetrating member and projects distally downward with respect to the head portion of the bone penetrating member. According to a further embodiment, a bone marrow access apparatus includes (i) a bone penetrating member including an internal channel having openings at proximal and distal ends of the bone penetrating member, (ii) a location member, and (iii) a coupling structure which couples the location member to the bone penetrating member such that the location member is at a distance proximal to the bone penetrating member.

Various aspects of the embodiments can be combined or used separately from each other, as will be appreciated from the description below.

BRIEF DESCRIPTION OF THE DRAWINGS

FIG. 17A is a front view of another cap of the bone marrow access apparatus according to the third embodiment;

FIG. 17B is a cross-sectional view taken along the line 17B-17B in FIG. 17A;

FIG. 18A is a front view of another cap of the bone marrow access apparatus according to the third embodiment;

FIG. 18B is a cross-sectional view taken along the line 18B-18B in FIG. 18A;

DETAILED DESCRIPTION

Figure 1:
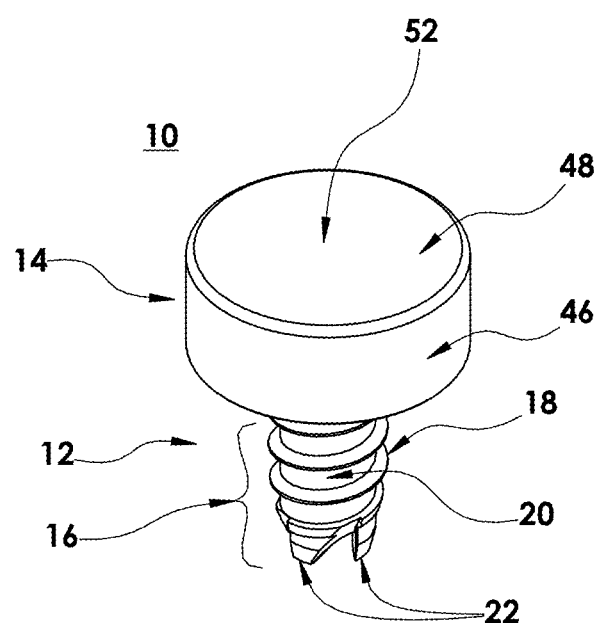
FIG. 1 is a perspective view of a bone marrow access apparatus according to a first embodiment.

In the following description and accompanying drawings, like reference numerals refer to the same or similar elements.

First Embodiment

Figure 4:
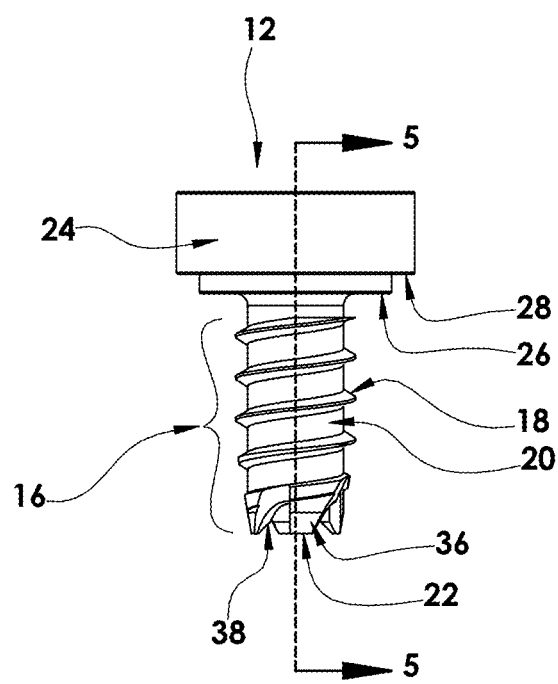
FIG. 4 is a front view of a bone penetrating member of the bone penetrating apparatus of the first embodiment.
Figure 5:
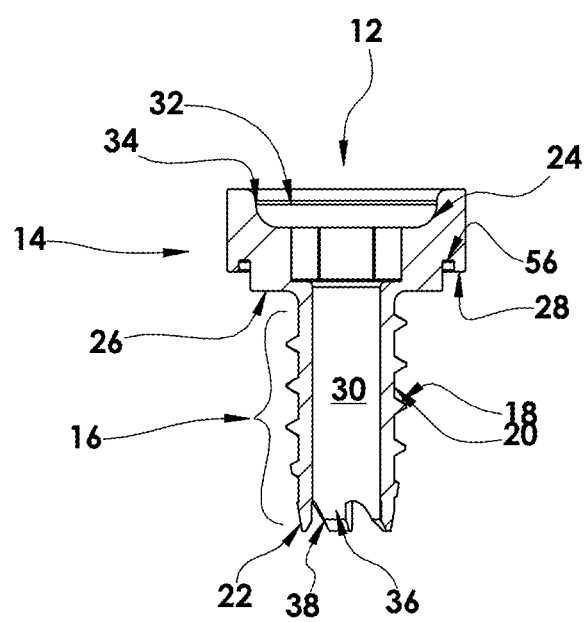
FIG. 5 is a cross-sectional view taken along the line 5-5 in FIG. 4.
Figure 6:
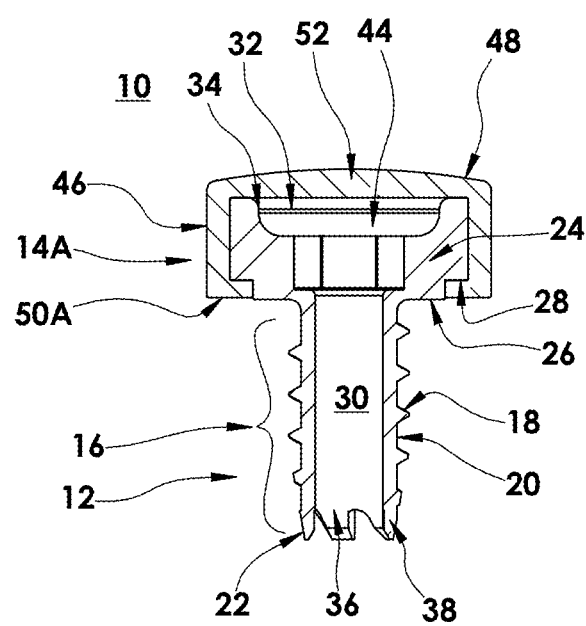
FIG. 6 is a cross-sectional view showing a modification of the first embodiment.

FIGS. 1-5 show a bone marrow access apparatus 10 in accordance with a first embodiment of the invention, and FIG. 6 shows a modification of the first embodiment. As shown in FIGS. 1-6, the bone marrow access apparatus 10 includes a bone penetrating member 12 and a cap 14. The bone penetrating member 12 is configured to penetrate into a bone across the bone cortex to enable access to a marrow space in the bone during use of the bone marrow access apparatus 10. The cap 14 is configured to control access to the marrow space through the bone penetrating member 12 and partly covers the bone penetrating member 12.

As shown in FIGS. 1-6, the bone penetrating member 12 includes an axially extending, substantially tubular insertion portion 16. The bone penetrating member 12 also includes a head portion 24 at the top (proximal) end of the tubular portion 16 (see FIGS. 3-5). The head portion 24 has a larger (wider) cross-sectional shape (and larger diameter when circular) than that of the insertion portion 16 (see FIG. 3). The head portion 24 may have a hexagonal cross-section or a circular cross-section in a plane perpendicular to the axial direction of the bone penetrating member 12, or may have other cross-sectional shapes such as square, triangle, Torx, and the like. The bone marrow access apparatus 10 is intended to be installed in connection with a bone, meaning here that only part of the bone marrow access apparatus 10 is situated in the bone (for example, the insertion portion 16 of the bone penetrating member 12) while another part is situated on, above and/or outside of the bone (for example, the head portion 24 of the bone penetrating member 12).

Other bone marrow access apparatuses described in the present application are installed in the same or a similar manner.

Figure 3:
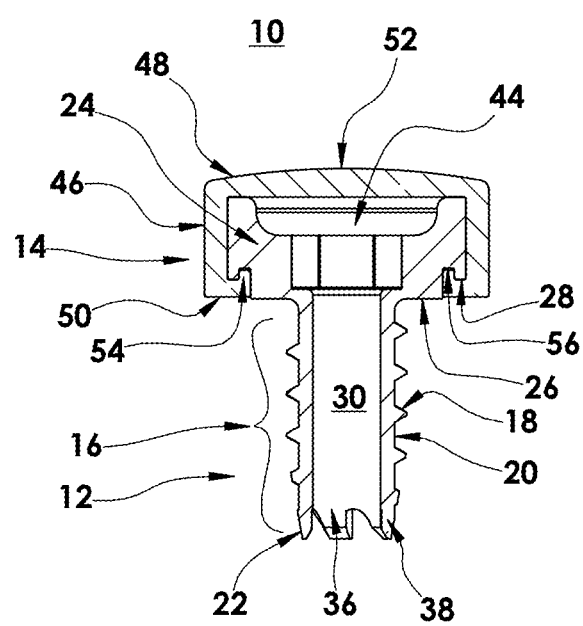
FIG. 3 is a cross-sectional view taken along the line 3-3 in FIG. 2.

As shown in FIGS. 3-5, the head portion 24 has a bottom (distal) surface 26 adjacent to and surrounding the insertion portion 16 and a step 28 peripherally outward of and surrounding the bottom surface 26. The step 28 is recessed upward (proximally) with respect to the bottom surface 26 of the head portion 24 to provide the outer peripheral surface of the head portion 24 with a peripheral indentation. The step 28, moreover, has a groove (recess) 56 projecting upward (proximally) from the bottom of the step 28 and extending around the entire step 28 (see FIG. 5). The head portion 24 may be configured without the step 28, so that the entire outer bottom (distal) portion of the head portion 24 is the bottom surface 26, and so that the groove 56 projects upward from the bottom surface 26 at a location between the insertion portion 16 and the outer peripheral edge of the bottom of the head portion 24.

Figure 2:
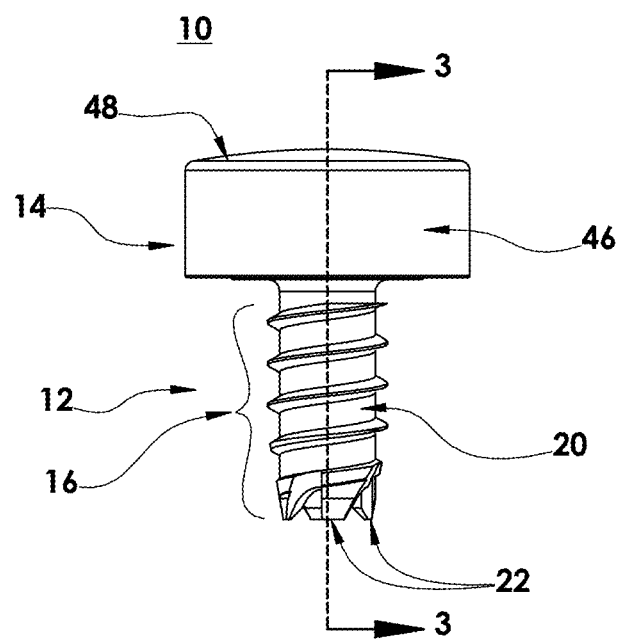
FIG. 2 is a front view of the bone marrow access apparatus shown in FIG. 1.

As shown in FIGS. 1-3, the cap 14 can be configured with one or more walls that define an interior cavity 44 dimensioned to accommodate at least part of the bone penetrating member 12, namely at least the head portion 24 as shown in FIG. 3. The cap 14 includes a peripheral wall 46 arranged peripherally outward of the head portion 24. When the cap 14 is operatively engaged with the bone penetrating member 12, the peripheral wall 46 may entirely surround the head portion 24 of the bone penetrating member 12. The peripheral wall 46 has an inner surface having generally the same cross-sectional shape (in a plane perpendicular to the axis of the bone marrow access apparatus 10) as the outer surface of the head portion 24. The interior cavity 44 defined by the cap 14 is sized to provide for a tight fit between the cap 14 and the bone penetrating member 12. For example, the area defined by the peripheral wall 46 may be slightly larger than the area defined by the outer periphery of the head portion 24 in the plane perpendicular to the axis of the bone marrow access apparatus 10.

As shown in FIGS. 2 and 3, in the first embodiment, the cap 14 also includes an upper wall 48 connected to an upper edge region of the peripheral wall 46 and extending inward and a lower wall or lower rim 50 connected to a lower edge region of the peripheral wall 46 and extending inward. When the cap 14 is engaged with the bone penetrating member 12, all or a significant part of the upper wall 48 is situated above the upper surface of the head portion 24 of the bone penetrating member 12 and all or a significant part of the lower rim 50 is situated in the step 28 and thus underlies a peripheral edge region of the head portion 24 of the bone penetrating member 12 (see FIG. 3). In this embodiment, the lower rim 50 extends around the entire outer periphery of the bone penetrating member 12, so as to engage with the entire step 28. The lower rim 50 includes a projection 54 located at an inward end side (an inner edge) of the lower rim 50. The projection 54 projects upward (proximally) from the inner edge of the lower rim 50 and is situated in the groove 56 when the cap 14 is engaged with the head portion 24 (see FIG. 3). In this embodiment, projection 54 extends around the entire outer periphery of the bone penetrating member 12, so as to engage with the entire groove 56. With this configuration, the cap 14 can be securely attached to the bone penetrating member 12.

The placement of the lower rim 50 on the step 28 also means that the lower rim 50 is interposed between a part of the head portion 24 of the bone penetrating member 12 and the surface of the bone, when the bone marrow access apparatus 10 is installed in bone. The lower rim 50 thereby provides a cushioning effect to the bone marrow access apparatus 10 with respect to the bone. The lower rim 50 is preferably made of a soft elastomer which can be compressed and thereby cushions impact of the head portion 24 of the bone penetrating member 12 against the bone surface.

Various constructions of the bone penetrating member 12 and cap 14 are envisioned to provide for secure retention of the cap 14 to the bone penetrating member 12 for installation and use of the bone marrow access apparatus 10. For example, as shown in FIG. 6, the groove 56 and projection 54 may be omitted. In this case, a cap 14A is secured to the bone penetrating member by engagement of the step 28 with a lower rim 50A, and by the fit of the cap 14A on the head portion 24 of the bone penetrating member 12 as discussed above. In addition, as noted above, the step 28 may be omitted, and the groove 56 can project upward from the bottom surface 26 of the head portion 24. In this case, the lower rim 50 can overlap all or part of the bottom surface 26 of the head portion 24, and the projection 54 may project from the lower rim 50 and engage with the groove 56 that projects from the bottom surface 26. In this configuration, the projection 54 can project from a portion of the lower rim 50 other than the inner edge, that is, from some position between the inner edge of the lower rim 50 and the outer end of the lower rim 50 where the lower rim 50 meets the peripheral wall 46. Still further, the step 28 and lower rim 50 may be configured so that they only partially extend around the bone penetrating member, instead of fully surrounding the bone penetrating member. The step 28 and lower rim 50 could be provided in several discontinuous segments around the circumference of the bone penetrating member 12. Similarly, the groove 56 and projection 54 may be configured so that they only partially extend around the bone penetrating member 12, instead of fully surrounding the bone penetrating member 12. The groove 56 and projection 54 could also be provided in several discontinuous segments around the circumference of the bone penetrating member 12. The groove 56 and projection 54 could also be located at a different position of the bone penetrating member 12 and cap 14. For example, the groove 56 could be provided in an outer peripheral surface of the head portion 24 of the bone penetrating member 12, and the projection 54 could project from the peripheral wall 46 of the cap 14. Moreover, instead of peripheral wall 46, upper wall 48 and/or lower rim 50, other structure for securing the cap 14 to the bone penetrating member 12, whether the head portion 24 or another part of the bone penetrating member 12, may be used in the invention. Alternative securing structures which perform the same function as the peripheral wall 46 and lower rim 50 in the same or similar manner are readily ascertainable by those skilled in the art to which this invention pertains and are considered to be within the scope of the invention. All such structures are considered to be encompassed within the phrase securing means for securing the cap to the bone penetrating member, which may be used herein.

In some embodiments, an important characteristic of the valve cap 14 is that at least the portion above the head portion 24 of the bone penetrating member 12, i.e., part or all of the upper wall 48, is made of atraumatic material. Soft elastomers known to be atraumatic may preferably be used. Use of atraumatic material prevents damage to the skin above the bone marrow access apparatus 10 when present in a human body. It is possible to form the cap 14 entirely from atraumatic material. Exemplifying characteristics of an atraumatic material include it being soft and having low durometer, with the purpose being to prevent skin erosion and degradation, and to provide a cushion layer between the skin and the bone penetrating member 12. On the other hand, in a preferred embodiment, the bone penetrating member 12 is made of a rigid biocompatible material. Suitable materials include, without limitation, stainless steel, titanium, nitinol, and polyetheretherketone (PEEK).

In the embodiment of FIGS. 1-5, and in the modification shown in FIG. 6, the upper wall 48 of the cap 14 includes or is formed by a septum 52 that self-heals. The septum 52 having this configuration may also be referred to as a self-healing membrane or self-healing septum 52. Self-healing in this context means that, after a bone marrow access instrument such as a sampling needle punctures the septum 52 during use of the bone marrow access apparatus 10 and is removed when the sampling is concluded, the septum 52 closes the opening made by the sampling needle and re-forms a seal to prevent flow of tissue in or out of the cortical layer. The self-healing property of the septum 52 could be provided or enhanced by structuring the cap 14 such that pressure is applied radially inwardly toward the center of the septum 52. The manner in which a self-healing septum 52 could be included in the upper wall 48 of the cap 14 is readily ascertainable by those skilled in the art to which this invention pertains in view of the disclosure herein, especially since the septum 52 and the upper wall 48 are made of the same material in preferred embodiments.

In the present embodiment, the bone marrow access apparatus 10 is installed by first drilling a hole (referred to herein as a pre-drilled hole or a pilot hole) into the bone of the patient, and then by hand-screwing the bone marrow access apparatus 10 into the pre-drilled hole. A tool that grips the outside of the bone marrow access apparatus 10 (such as the outside of the cap 14) could be used to assist in screwing the bone marrow access apparatus 10 into the bone. As shown in FIGS. 1-6, the substantially tubular insertion portion 16 of the bone penetrating member 12 has a spiral thread 18 on its outer surface 20. The spiral thread 18 enables the bone penetrating member 12 to be urged into the bone cortex (in the pilot hole) upon rotation of the bone penetrating member 12. That is, the spiral thread 18 enables the insertion portion 16 to be tapped or screwed into the bone cortex, and also provides for secure retention of the insertion portion 16 in the bone cortex. The bone marrow apparatus 10 can thereby be securely retained in its use position in the bone. At the bottom (distal) end of the tubular portion 16, an exterior surface of the insertion portion 16 can be provided with fluted edges 22 to help cut into the bone cortex during installation of the bone marrow access apparatus 10. Fluted edges 22 may be omitted. Instead of a spiral thread 18 and/or fluted edges 22, alternative structures may be provided on the outer surface 20 and bottom end of the insertion portion 16 that function to enable insertion of the bone penetrating member 12 into the bone cortex and retention therein. Such alternative structure is known to those skilled in the art to which this invention pertains, and all such structures that enable the insertion portion 16 to be inserted in, engage with, and be retained in a bone are considered to be encompassed within the phrase insertion and retention means, which may be used herein. Removal of the bone marrow access apparatus 10, when it is no longer needed, could also be accomplished by hand or using a tool that grips the outside of the bone marrow access apparatus 10 (such as the outside of the cap 14). Alternatively, a tool could be inserted through the septum 52 to engage with a seat inside the bone penetrating member 12, so as to allow the bone penetrating member 12 to be unscrewed from the bone using the tool. The use of a tool in connection with the bone marrow access apparatus 10 is discussed in more detail below. In this embodiment, a tool would preferably be used while inserted through the septum 52 only for removal (not insertion) of the bone penetrating member 12, because the tool may damage the septum 52 beyond its capacity for self-healing. Self-healing of the septum 52 is not a concern when the bone marrow access apparatus 10 is being removed.

As shown in FIGS. 3, 5, and 6, an internal channel 30 extends through the bone penetrating member 12, from a proximal end 34 of the internal channel 30 at an opening 32 in the upper surface of the head portion 24, to a distal end 38 of the internal channel 30 at an opening 36 in the bottom of the insertion portion 16. Through channel 30, bone marrow can be removed from the marrow space in the bone when the bone marrow access apparatus 10 is inserted in and engaged with the bone. Removal of bone marrow from the marrow space is commonly referred to as bone marrow sampling. Other uses of the bone marrow access apparatus 10 and its internal channel 30 will be apparent to those of skill in the art. For example, fluid can be delivered to a patient through the internal channel 30. Delivery of fluids and drugs, such as chemotherapeutic agents, into the marrow is disclosed in "Induction treatment of acute myeloid leukemia in an elderly patient with intramarrow injection/administration of cytarabine: first report of a case", by Anwarul Islam, Clinical Case Reports, 2015, pages 1026-1029. Additionally, Dr. Valerie A. Rosetti et al. discuss intraosseous infusion through the tibia in children in "Intraosseous Infusion: An Alternative Route of Pediatric Intravascular Access", Annals of Emergency Medicine, 14:9 Sep. 1985.

Internal channel 30 has a particular size to enable bone marrow sampling when the bone marrow access apparatus 10 is in use. The channel 30 may have a diameter in a range from about 2.0 mm to about 4.2 mm (8-15G) to allow for insertion of large-sized needles and other types of standardly used sampling instruments. The dimensions of the channel 30, i.e., its length and diameter, may also be selected to enable tilting of a sampling needle to allow it to reach fresh areas of the marrow space after repeated sampling. The degree of tilting of the needle is thus dependent on the diameter of the needle, the diameter of the channel 30, and the length of the channel 30. In one embodiment, the channel 30 is dimensioned to enable a needle having a size of 13G to tilt while in the channel by about 15 degrees in all directions relative to a central axis of the channel 30, thereby providing a total degree of tilt of about 30 degrees. In another embodiment, the channel 30 is dimensioned to enable a needle having a size of 15G to tilt by about 10 degrees to each side, thereby providing a total degree of tilt of about 20 degrees. The 15G needle may be used to sample cells via needle aspiration, while the 13G instrument retrieves worm-like tissue samples and benefits more from tilting to source a fresh sampling area. Of course, different combinations of differently sized needles and channels 30 provide different tilt angles. A medical practitioner using bone marrow access apparatus 10 may be apprised of the needle sizes that can be used with each size of bone marrow access apparatus 10 and the obtainable tilt angles. In addition, other sizes of needles may be appropriate for other uses of the bone marrow access apparatus 10. For example, if the bone marrow access apparatus 10 is used to deliver or infuse fluid, then a 21-25G needle may be appropriate.

The axial length of the insertion portion 16 of the bone penetrating member 12 is dimensioned to at least reach the marrow space of a particular bone when the head portion 24 is on the surface of the bone. Thus, there may be a plurality of different heights of insertion portions 16 of bone penetrating members 12, and a suitable height is selected based on the bone on which the bone penetrating member 12 is being installed and possibly also the size of the bones of the patient. Moreover, the height of the insertion portion 16 and the dimensions of the thread 18 are selected to enable retention of the bone penetrating member 12 in the bone.

For example, the insertion portion 16 can have a relatively short height when the bone marrow access apparatus 10 will be installed at a position where the distance from the bone surface to the bone marrow space is short. In one example, the height of the insertion portion 16 is about 0.62 inches, and the height of the cap 14 is about 0.28 inches, providing the bone marrow access apparatus 10 with an overall height of about 0.90 inches. In another example, the height of the insertion portion 16 is only about 0.52 inches, and the height of the cap 14 is about 0.28 inches, providing the bone marrow access apparatus 10 with an overall height of about 0.80 inches. In other words, an overall height of the bone marrow access apparatus 10 of 0.90 inches or less, or 0.80 inches or less, can be achieved. These exemplary dimensions are not limiting in any manner, and are provided to exemplify the possibility of providing a shorter height of the insertion portion 16 of the bone penetrating member 12 to address shorter thickness bones.

In the embodiment discussed above, the bone penetrating member 12 and cap 14 are shown as being formed as separate components and are engaged with one another in a secure manner for use of the bone marrow access apparatus 10. This engagement of the bone penetrating member 12 and cap 14 can be performed at a manufacturing stage, before supplying the bone marrow access apparatus 10 to a purchaser or end user (e.g., a physician). Accordingly, the bone marrow access apparatus 10 can be supplied to the user as a single, integrated unit. In such an embodiment, the bone penetrating member 12 may be considered a bone penetrating part of the unit while the cap 14 is considered a covering part of the unit. The connection of the bone penetrating member 12 and cap 14 can be achieved by inserting the head portion 24 of the bone penetrating member 12 through an opening defined by the lower rim 50 into the interior cavity 46 until the lower rim 50 has been urged into the step 28 in the head portion 24 and the projection 54 urged into the groove 56. The head portion 24 should fit snugly into the interior cavity 44 defined by the cap 14. Other bone marrow access apparatuses described in the present application are or may be pre-assembled in the same or a similar manner.

It is also envisioned that the bone penetrating member 12 and cap 14 may be supplied to the end user as separate elements. In this case, the bone penetrating member could be inserted (screwed) into bone with the use of a tool as described below with respect to the second embodiment, with or without pre-drilling a hole for the bone penetrating member. Once the bone penetrating member 12 is substantially or fully screwed into the bone, the cap 14 could be placed over the head portion 24 of the bone penetrating member, and the projection 54 (if present) could be engaged with the groove 56 (if present) at that time.

It is possible to use the bone penetrating member 12 without the cap 14. In other words, the bone penetrating member 12 shown in FIGS. 4 and 5 can be used as a bone marrow access apparatus on its own, without cap 14. When the bone penetrating member is used without the cap 14, the bone penetrating member 12 can be installed in a bone using a pre-drilled hole as described above or by using a tool as described below with respect to the second embodiment, with or without pre-drilling a hole for the bone penetrating member 12. Various use of the bone penetrating member 12 without a cap 14 are readily ascertainable to those skilled in the art to which this invention pertains in view of the disclosure herein. Thus, bone penetrating member 12 may thus be used alone, with cap 14, or possibly with or in other apparatuses.

Second Embodiment

Figure 9:
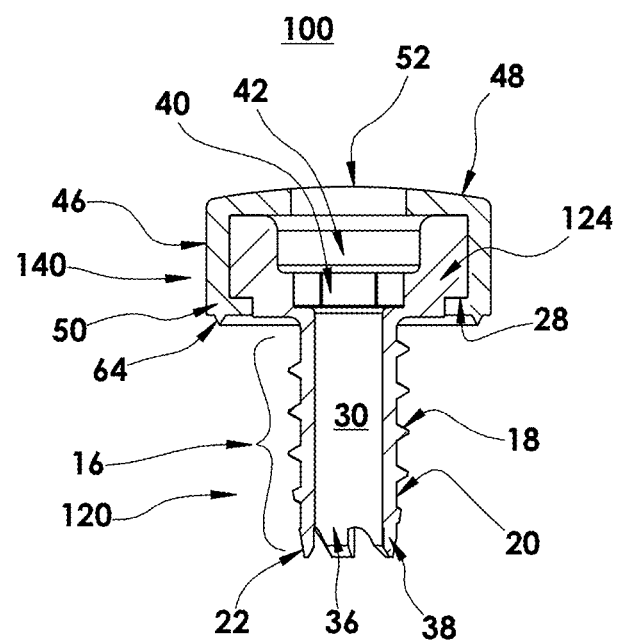
FIG. 9 is a cross-sectional view taken along the line 9-9 in FIG. 8.
Figure 10:
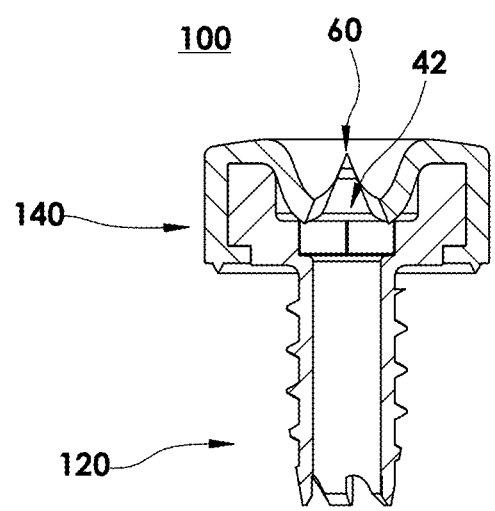
FIG. 10 is a cross-sectional view showing a valve of the bone marrow apparatus shown in FIG. 7 in an open state.
Figure 11:
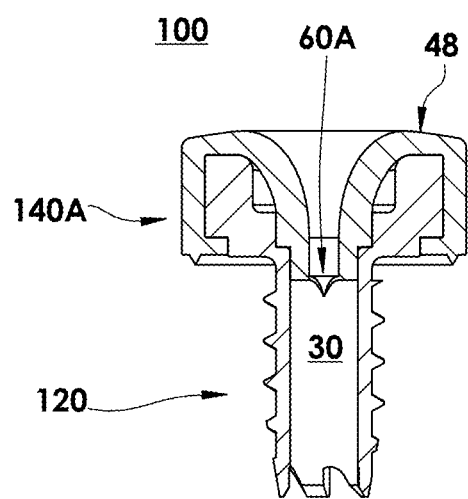
FIG. 11 is a cross-sectional view showing a modification of the second embodiment.

FIGS. 7-10 show a bone marrow access apparatus 100 in accordance with a second embodiment of the invention, and FIG. 11 shows a modification of the second embodiment. As shown in FIGS. 7-10, the bone marrow access apparatus 100 includes a bone penetrating member 120 and a cap 140.

The bone penetrating member 120 is substantially the same as the bone penetrating member 12 of the first embodiment, except that the interior space (a valve relief space 42) of the head portion 124 of the bone penetrating member 120 is deeper than the corresponding space in the head portion 24 of the bone penetrating member 12 of the first embodiment. In addition, in the bone penetrating member 120, part of the internal channel 30 is formed as a seat 40 below the upper surface of the head portion 124 (see FIG. 9). The seat 40 is designed to cooperate with one or more tools to enable the bone penetrating member 120 to be screwed into the bone and to facilitate removal of the bone marrow access apparatus 100 from the bone, as described in more detail below. The seat 40 may also be present in the first embodiment (see FIGS. 3, 5, and 6) and may be used, for example, to install the bone penetrating member 12 in bone when the bone penetrating member is used alone, without cap 14, and/or to remove the bone penetrating member 12 after use of the bone marrow access apparatus is complete.

The cap 140 has substantially the same features as cap 14 of the first embodiment, with three notable exceptions. First, the upper wall 48 includes a valve 60 situated entirely above the bone penetrating member 120, instead of the septum 52 of the first embodiment. Accordingly, the cap 140 may be referred to as a valve cap. Second, the cap 140 has a projection 64 at its bottom surface. Third, the cap 140 may be taller than the cap 14 of the first embodiment.

Various aspects of the first and second embodiments can be combined with each other or used in place of each other. For example, as shown in FIG. 9, the head portion 124 of the bone penetrating member has the step 28 but not the groove 56 shown in FIG. 3, and the cap 140 in the second embodiment has the lower rim 50 but not the projection 54 of the first embodiment shown in FIG. 3. That is, bottom of the head portion 124 corresponds in shape to the bottom of the head portion 24 shown in FIG. 6. However, the head portion 124 of the second embodiment may include the groove 56 of the first embodiment shown in FIG. 3, and the cap 140 of the second embodiment may include the projection 54 shown in FIG. 3. The groove 56 and projection 54 can engage with each other to further secure the cap 140 to the bone penetrating member 120 in the same manner as in the first embodiment. In addition, the projection 64 of the cap 140 of the second embodiment can be used with the cap 14 of the first embodiment.

Figure 7:
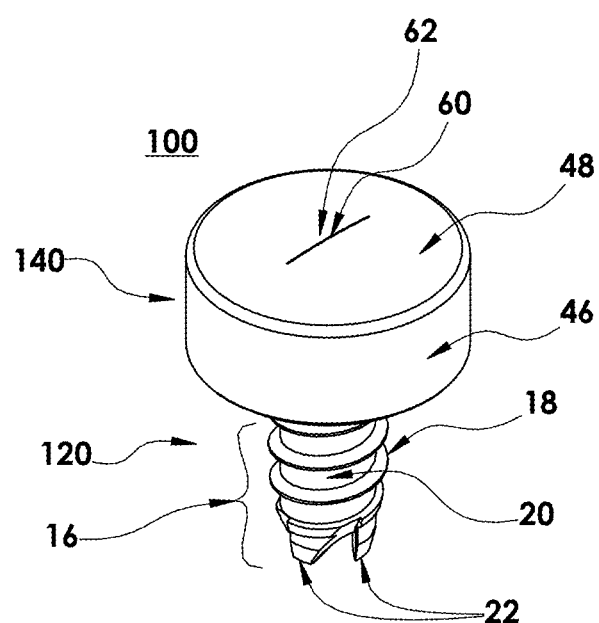
FIG. 7 is a perspective view of a bone marrow access apparatus according to a second embodiment.
Figure 8:
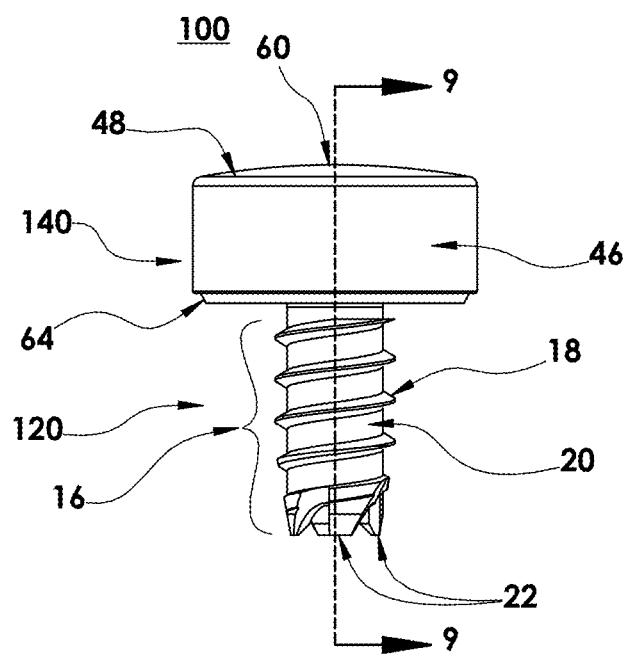
FIG. 8 is a front view of the bone marrow access apparatus shown in FIG. 7.

As shown in FIGS. 7, 8, and 10, the valve 60 has an opening 62 that controls access to the channel 30. That is, valve 60 in a closed state does not allow the flow of tissue in and out of the bone, and thereby, for example, prevents leakage of marrow from the bone marrow access apparatus 100. The valve opening 62 is closed in a default state, which closes the channel 30 of the bone penetrating member 120 and prevents the flow of material into and out from the bone marrow access apparatus 100. The valve opening 62 can be opened to an open state (see FIG. 10) by inserting, for example, a sampling needle through the valve opening 62 and into the channel 30.

Valve 60 has a construction to enable the valve opening 62 to be repeatedly switchable between the open and closed states. For example, the valve 60 may be a single slit valve as shown in FIG. 7, or alternatively, an intersecting or cross slit valve. Such slit valves have leaflets that contact one another in a default closed state and must be urged apart from one another to form the opening. When urged apart from one another, for example, by a sampling needle being introduced into and through the channel 30 into the marrow space in the bone, the leaflets are pushed inward into the channel 30 during use of the bone marrow access apparatus 100 and accommodated in the valve relief space 42 in the head portion 124 of the bone penetrating member 120.

Instead of a slit valve as shown in FIG. 7, the valve 60 may be a duck-bill valve. In addition, as shown in FIG. 7, the cap 140 includes only a single valve, but the cap 140 can include more than one valve. Generally, the valve 60 is designed for repeated opening and closing of the opening 62, without losing integrity or releasing fragments thereof. The manner in which the valve 60 could be included in the upper wall 48 of the cap 140 is readily ascertainable by those skilled in the art to which this invention pertains in view of the disclosure herein, especially since the valve 60 and the upper wall 48 of the cap 140 are made of the same material in preferred embodiments.

It is also envisioned that, in a modification of the second embodiment shown in FIG. 11, a valve 60A may be situated in a part of cap 140A other than in the upper wall 48. For example, as shown in FIG. 11, the valve 60A may be invaginated (or recessed) into the channel 30 of the bone penetrating member 120.

Valve 60 (or 60A) is generally representative of an access control component that controls access to the channel 30. Other access control components that perform the same functions as the valve 60 described herein may be used as alternatives to the valve 60. Such alternative access control structures and tissue flow prevention structures that perform the same function as the valve 60 in the same or a similar manner are readily ascertainable by those skilled in the art to which this invention pertains and are considered to be within the scope of the invention. A valve and all such comparable access control components are considered to be encompassed within the phrase access control means (for controlling access to the channel 30), which may be used herein.

As shown in FIG. 9, in the bone marrow access apparatus 100, part of the internal channel 30 is formed as the seat 40 below the upper surface of the head portion 124. The seat 40 is designed to cooperate with one or more tools to enable the bone penetrating member 120 to be screwed into the bone and to facilitate removal of the bone marrow access apparatus 100 from the bone. See, for example, WO 2018/067525, which is incorporated herein by reference. The seat 40 may have a particular shape or construction to enable rotation of a tool to impart rotation of the bone penetrating member 120 when the tool is mated with the seat 40 of the bone penetrating member 120. For example, a polygonal, e.g., hexagonal shape, for the seat 40 with a corresponding hexagonal shape for a flange of the tools is possible.

Prior to installation (generally, but not necessarily, at a manufacturing stage), the bone penetrating member 120 and the cap 140 are assembled to form the bone marrow access apparatus 100, as described above with respect to the first embodiment. In order to install the bone marrow access apparatus 100, a delivery tool (see WO 2018/067525) is inserted through the opening 62 of the valve 60 and mated with the seat 40 of the bone marrow access apparatus 100. The delivery tool, with the attached bone marrow access apparatus 100, is guided through an incision in the patient's skin to insert the insertion portion 16 of the bone penetrating member 120 into a pilot hole which has been drilled in the bone. Instead of using a pilot hole, the delivery tool and bone marrow access apparatus 100 can be configured to provide for a self-tapping insertion. Insertion of the bone penetrating member 120 into the bone is aided by the thread 18 on the outer surface 20 of the insertion portion 16 of the bone penetrating member 120. When a pilot hole is used, the thread 18 grips the surface of the bone cortex defining the pilot hole. The tool is rotated to cause the bone penetrating member 120 to be further inserted into the bone. Rotation of the tool continues until a channel through the bone cortex into the marrow space is completed and the lower surface of the lower rim 50 of the cap 140 rests on the surface of the bone. After the bone marrow access aperture 100 is installed, the tool is removed from engagement with the bone marrow access apparatus 100 by lifting it upward and removing it through the opening 62 of the valve 60, causing the opening 62 to close. The tissues above the apparatus 100 are then surgically closed. Note that glue or another adhesive is not required to install the bone marrow access apparatus 100. Once the bone marrow access apparatus 100 is installed in connection with a bone, it can be used for sampling bone marrow whenever such sampling is desired either for biopsy or aspiration, dependent on which instrument is used.

Installation of a bone marrow access apparatus is described in detail in WO 2018/067525. To the extent that bone marrow access apparatuses discussed in WO 2018/067525 differ from the bone marrow access apparatus 100 (and/or other bone marrow apparatuses as described in the present application), one of ordinary skill would understand how to adapt the techniques discussed in WO 2018/067525 to the bone marrow access apparatuses described in the present application.

As described above, during installation the delivery tool is inserted through the opening 62 of the valve 60 and mated with the seat 40 of the bone marrow access apparatus 100. The leaflets of the valve 60 are pushed inward (distally) by the tool and are accommodated in the valve relief space 42 in the head portion 124 of the bone penetrating member 120 (see FIG. 10, showing the position of the valve leaflets in an open state). In order to accommodate the leaflets, the valve relief space 42 is larger than the corresponding space in the bone penetrating member 12 of the first embodiment. For example, the valve relief space 42 may be about 0.08 inches deeper for the bone penetrating member 120 used with the valve cap 140 than the corresponding space in the bone penetrating member 12 used with the cap 14 (which lacks a valve). The larger valve relief space 42 enables the leaflets of the valve 60 to snap back proximally after insertion of a tool into engagement with the seat 40 in order to press against and hold the tool. The pressure of the leaflets of the valve 60 against the tool helps keep the tool in engagement with the seat 40, including while the tool rotates the bone penetrating member 120 into the bone. The dimensions of the valve relief space 42 may be determined based on the parameters of the valve 60 and the leaflets thereof, as well as the dimensions of the seat 40 and the tools used with the seat 40. In the present embodiment, for example, due to the valve relief space 42, the height of the cap 140 is about 0.34 inches (which is taller than the cap 14 in the first embodiment). The insertion portion 16 of the bone penetrating member 120 has a length of, for example, about 0.63 inches, providing the bone marrow access apparatus 100 with an overall height of about 0.97 inches. An insertion portion 16 with a height of about 0.52 inches or 0.62 inches may also be used.

To improve installation of the bone marrow access apparatus 100 on a bone, a projection 64 extends downward from the lower surface of the cap 140 toward the distal end of the channel 30, below the lower rim 50 (the lower rim 50 includes the portion of the cap 140 below the peripheral wall 46). The projection 64 may extend around the entire circumference of the cap 140, or may extend only partly around the circumference of the cap 140. The projection 64 may, as shown in FIG. 9, be provided below only part of the lower rim 50, or may be wider so as to be provided across all or substantially all of the lower rim 50 (the lower rim 50 includes the portion of the cap 140 below the peripheral wall 46). Moreover, instead of a single projection 64, multiple circumferential segments of the projection 64 may be provided instead with spaces therebetween.

The projection 64 has a substantially triangular cross-section (see FIG. 9). The triangular form of the projection 64 provides the installer of the bone marrow access apparatus 100 with a sensory indication (tactile feedback) regarding suitable installation of the bone marrow access apparatus 100 since the projection 64 will increase resistance to the insertion of the bone marrow access apparatus 100 as the projection 64 engages the bone. Accordingly, the projection 64 may be referred to herein as a tactile feedback member. Specifically, during installation of the bone marrow access apparatus 100, the bone penetrating member 120 will be screwed into the bone by rotating the insertion tool engaged with the bone penetrating member 120, and the tip of the triangular projection 64 will eventually contact the surface of the bone. After this point, continued rotation of the insertion tool will cause more material of the projection 64 to be compressed, resulting in greater difficulty in continuing rotation the insertion tool and further inserting the bone marrow access aperture 100. This difficulty indicates that the bone marrow access aperture 100 is appropriately installed on the bone.

Instead of the projection 64 having a triangular form, a tactile feedback member may be provided with an alternative form that serves to direct energy during installation of the bone marrow access apparatus 100 to provide a more tactile feedback than an otherwise flat lower surface of the cap 140, so as to signal to the installer of the bone marrow access apparatus 100 that the appropriate installation state is approaching and is then reached. The installer can thus stop rotating the insertion tool, and consider the bone marrow access aperture 100 to be appropriately installed on the bone.

Third Embodiment

Figure 12:
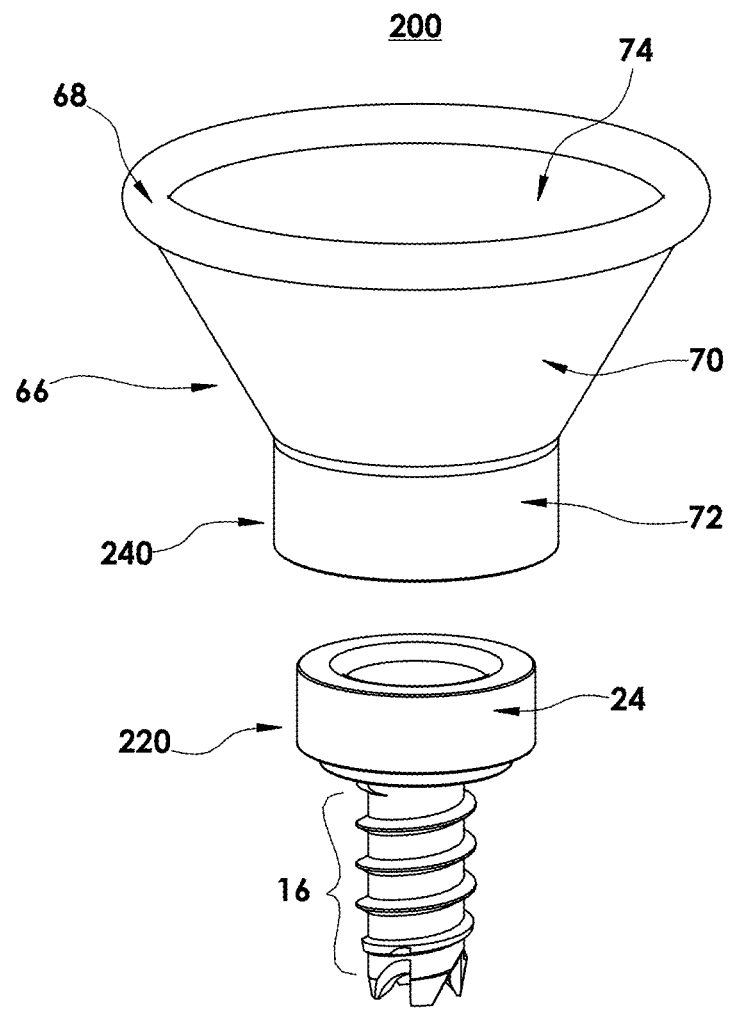
FIG. 12 is a perspective, exploded view of a bone marrow access according to a third embodiment.
Figure 13:
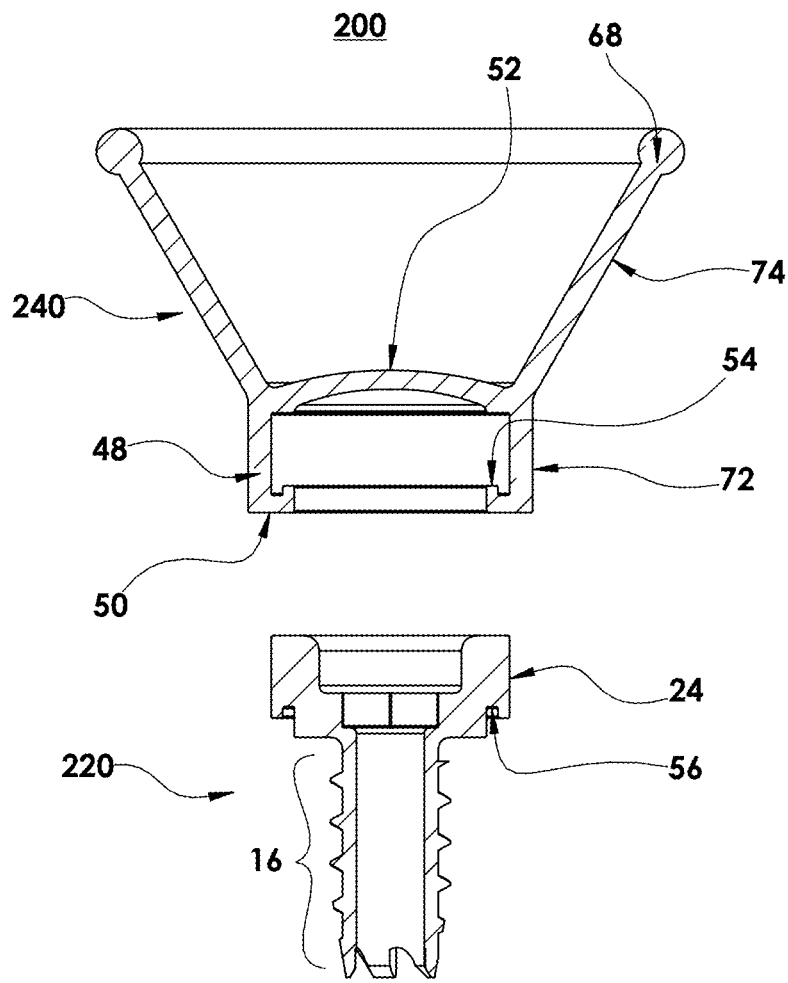
FIG. 13 is a cross-sectional, exploded view of the bone marrow access according to the third embodiment.
Figure 14:
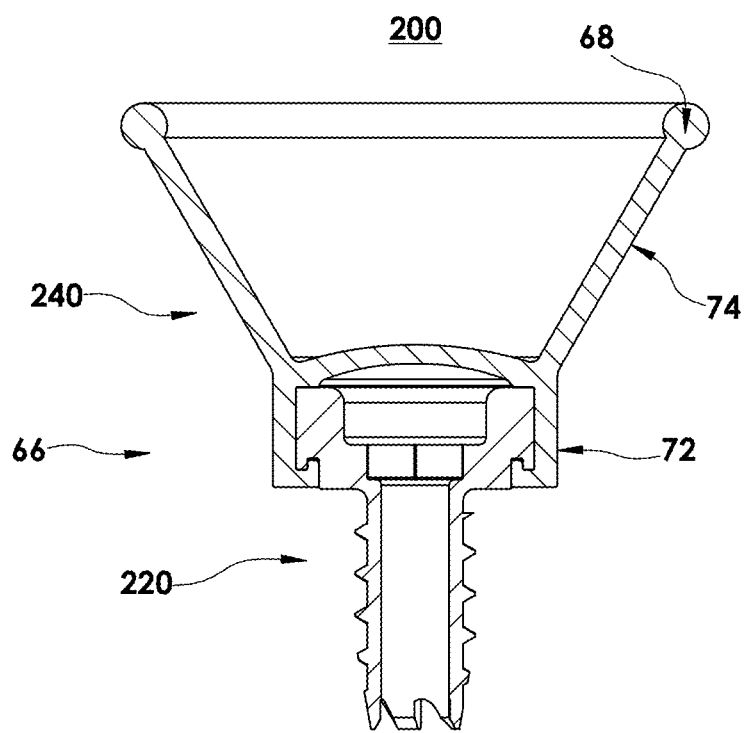
FIG. 14 is a cross-sectional view of the bone marrow access according to the third embodiment in an assembled state.
Figure 15:
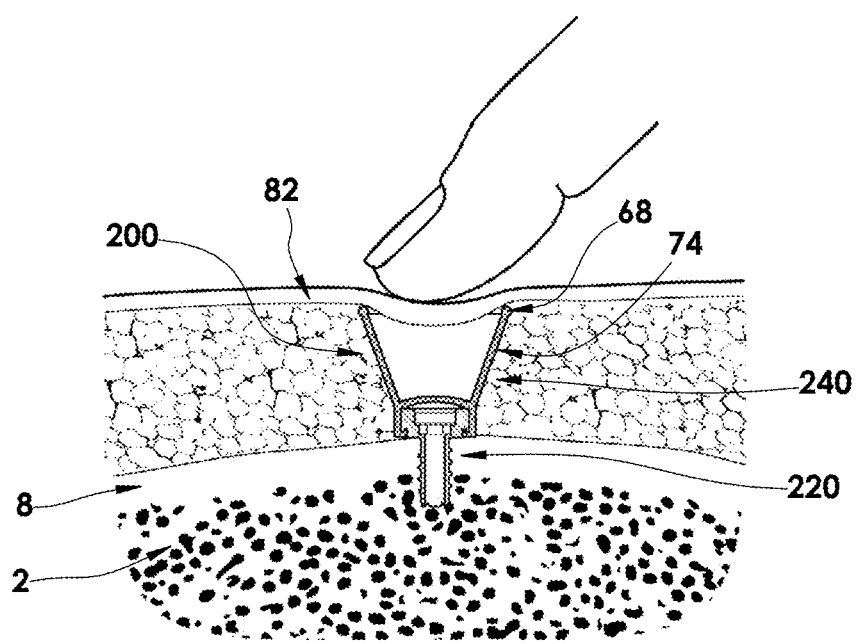
FIG. 15 is a cross-sectional view of the bone marrow access apparatus according to the third embodiment in an installed state and during a locating procedure.

FIGS. 12-20 show a bone marrow access apparatus 200 in accordance with a third embodiment of the invention. As shown in FIGS. 12-14, the bone marrow access apparatus 200 includes a bone penetrating member 220 and a cap 240.

The bone penetrating member 220 substantially corresponds to the bone penetrating member 12 of the first embodiment. As shown in FIGS. 13 and 14, unlike the bone penetrating member 12 of the first embodiment, the bone penetrating member 220 includes the valve relief space 42 and seat 40 described above with respect to the second embodiment. The valve relief space 42 and seat 40 are shown for illustrative purposes only (to illustrate aspects of the second embodiment being combined with aspects of the first embodiment), and can be omitted. That is, the bone penetrating member 220 can be identical to the bone penetrating member 12 of the first embodiment. The bone penetrating member 220 can have other configurations, such as the configuration of the bone penetrating member 120 of the second embodiment (with the cap 240 being appropriately modified to fit the bone penetrating member).

The cap 240 differs from the cap 14 of the first embodiment in that the cap 240 includes an extension 66 that extends from the upper portion of a structure corresponding to cap 14. The extension 66 aids a user (e.g., a physician) in locating the bone marrow access apparatus 200 under the skin (see FIG. 15). Cap 240 with the extension 66 is particularly useful when the distance between the upper surface of the cap 14 of the first embodiment and the skin would be greater than about 2.0 cm. At this depth, tactile feel of the cap 14 is diminished. As a result, the cap 14 is not easily palpable, and the cap 14 is difficult to locate when it is sought in order to, for example, sample bone marrow. (Methods of locating the bone marrow access apparatus other than by touch are possible, however, as discussed below with respect to FIGS. 42-53.)

The extension 66 generally includes a location member 68 (which can allows tactile location, i.e., location by touch, and also visual location at least in some situations) and a coupling structure 70 that couples the location member 68 to one or more of the peripheral wall 46, the upper wall 48, and the lower wall or rim 50 of the cap 240. The combination of these walls 46, 48, and 50 of the cap 240 (which have the same structure as the parts labeled with the same numbers in cap 14 of the first embodiment) will be referred to as a bone penetrating member engagement portion 72 of the cap 240. Although the present embodiment is described in terms of the extension 66 being provided in addition to the structure of the cap 14 of the first embodiment, the extension 66 can also be provided in addition to the structure of the cap 140 (the valve cap) of the second embodiment. The extension 66 can also be used in combination with modifications to the caps of the first and second embodiments, including configurations which combine features of the first embodiment (such as the projection 54) with features of the second embodiment (such as the valve 60 and/or projection 64).

Generally, location member 68 is elevated above the bone penetrating member engagement portion 72 to provide a structure closer to the skin than the bone penetrating member engagement portion 72. The location member 68 is fixed in position relative to the bone penetrating member engagement portion 72, which enables the septum 52 (or valve 60) to be easily located. When the extension 66 is used in connection with the valve cap 140, for example, it is possible to align the valve 60 with an approximate center of the location member 68 so that by locating the center of the location member 68, the center of the valve 60 is discernible. The septum 52 may be penetrated almost anywhere so locating its center is not as important.

The location member 68 is shown as a ring in FIG. 12, but other shapes of annular structures are also envisioned. The ring may be made of a hard or soft material, such as various thermoplastics or soft polymers. As used herein, annular means that the location member 68 is a closed structure with an interior opening, with the shape of the closed structure not being limited to a circular structure as shown and encompassing other closed structures, such as ellipses.

Coupling structure 70 can have different configurations. In FIGS. 12-15, the coupling structure 70 is a truncated conically shaped wall 74 that extends upward and outward from an outer edge of the upper surface of the bone penetrating member engagement portion 72 (from the region where the peripheral wall 46 and upper wall 48 meet). The location at which the conical wall 74 extends from the bone penetrating member engagement portion 72 is not critical to the invention and may vary from the region where the peripheral wall 48 and upper wall 50 meet (see FIGS. 16A-19B described below). In this embodiment, the location member 68, coupling structure 70 and bone penetrating member engagement portion 72 have a unitary construction. This means that the location member 68, coupling structure 70 and bone penetrating member engagement portion 72 are formed as a single unit or single piece. Extension 66 may be considered an extension part of this unitary construction. A unitary extension and bone penetrating member engagement portion may be referred to as a cone cap. Extension 66 can be entirely made of substantially the same soft polymer or elastomer as the bone penetrating member engagement portion 72. For example, the extension 66 may be made of silicone or polyurethane. Other materials may be used, as would be readily determinable by one skilled in the art to which this invention pertains in view of the disclosure herein. In this connection, the coupling structure 70 should not be stiff under skin, to prevent injury of a patient in which the bone marrow access apparatus 200 is installed if they should fall on it, and the location member 68 should be firm to enable it to be easily located and grasped. The location member 68 and coupling structure 70 may therefore be made of different materials.

Thus, the truncated conically shaped wall 74 may be fabricated from a soft material. The durometer of the truncated conical wall 74 is selected in consideration of various characteristics. First, the truncated conical wall 74 should not be overly rigid because it might harm a patient in which the bone marrow access apparatus 200 is installed if they should fall on it. In other words, the truncated conical wall 74 is preferably collapsible in the event that the patient falls on it. On the other hand, the truncated conical wall 74 cannot be too soft since it should be able to form a stable conduit through which a physician can insert a sampling needle when sampling bone marrow using the bone marrow access apparatus 200. Moreover, the truncated conical wall 74 should preferably not be so soft as to be easily punctured by a sampling needle. Various ranges of durometer are possible for the truncated conical wall 74, e.g., from 5 to about 50 Shore A, from about 20 to about 70 Shore A, from about 40 to about 70 Shore A. One skilled in the art would be able to determine a suitable durometer of the truncated conical wall 74 based on the requirements disclosed herein. In general, the material from which the coupling structure 70 including the truncated conical wall 74 is made should be flexible and soft in a radial dimension, but somewhat rigid in the axial dimension. This axial or column strength prevents the extension 66 from collapsing when it is pushed down by a finger or fingers during the locating procedure, and thereby provides a tactile response. A preferred durometer is from about 30 Shore A to about 50 Shore A, providing a soft yet stiff coupling structure 70.

The angle of attack of the interior surface of the conical wall 74 is preferably designed to be sufficiently steep to minimize the occurrence of a needle skiving material from the conical wall 74 as the needle is advanced distally during bone marrow sampling. (The angle of attack is described herein with reference to the conical angle of the truncated conical wall 74.) During sampling, the physician may squeeze the truncated conical wall 74 to form a conduit and can determine a straight path through the location member 68 to the septum 52 (or valve 60). A smaller angle of attack (conical angle) requires less squeezing to form a suitable conduit for the needle. Any conical angle between about 20 degrees and 60 degrees may be provided for the truncated conical wall 74 in the extension 66. In a range from about 20 degrees to about 30 degrees, it was found that the sampling needle was not skiving material off of the coupling structure 70. The height of the truncated conical wall 74 is also variable to accommodate different distances between the bone and skin of different patients.

Moreover, a strengthening structure, such as one or more ribs, may be included in the extension to provide additional column strength. As such, different caps 240 are envisioned with different conical angles of the truncated conical wall, different heights of the truncated conical wall, and with or without ribs providing column strength to the truncated conical wall. FIGS. 16A-19B illustrate various such examples of the structure of the cap 240 shown in FIGS. 12-15. In this connection, it is envisioned that caps 240 provided with ribs may be formed from a softer material than caps 240 provided without ribs, because the ribs provide extra strength to the cap 240.

Figure 16B:
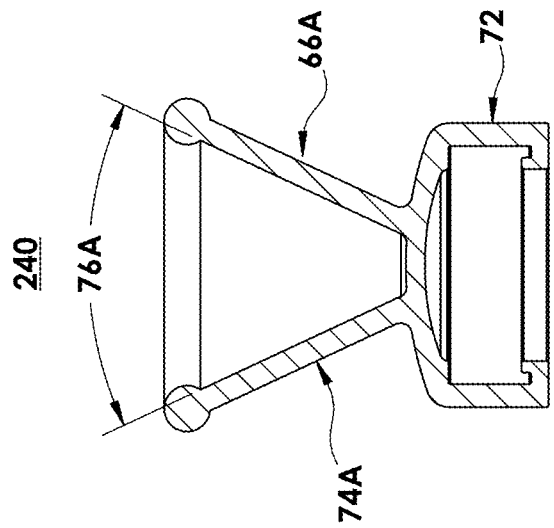
FIG. 16B is a cross-sectional view taken along the line 16B-16B in FIG. 16A.
Figure 16A:
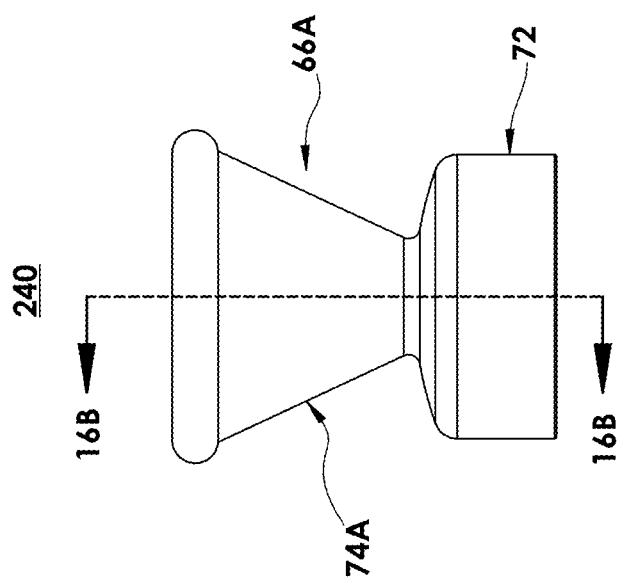
FIG. 16A is a front view of a cap of the bone marrow access apparatus according to the third embodiment.

FIGS. 16A and 16B show a cap 240 having an extension 66A and bone penetrating member engagement portion 72 having a unitary or integral construction and in which a truncated conical wall 74A of the extension 66A is relatively short (height of about 1 inch) and extends upward and outward from a region inward of the outer edge of the upper wall 48. This region may be immediately outward of the valve 60 without obstructing the valve opening 62 (when the valve 60 and valve opening 62 are present). Extension 66A does not include ribs and its conical angle 76A is about 50 degrees.

Figure 17C:
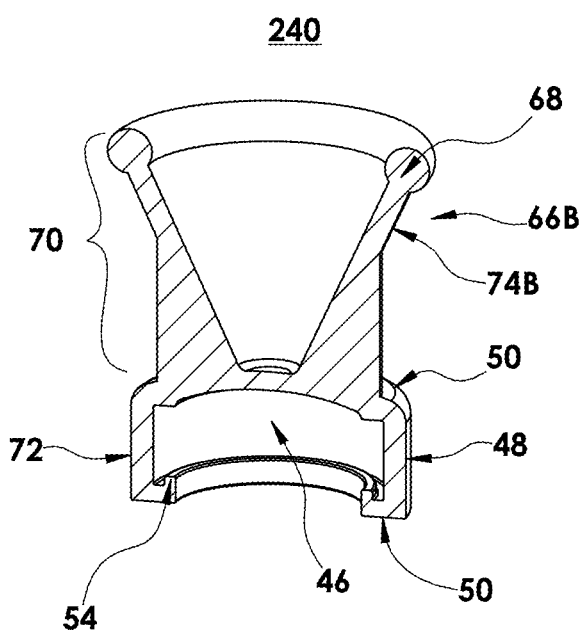
FIG. 17C is a perspective cross-sectional view taken along the same line as FIG. 17B.

FIGS. 17A, 17B, and 17C show a cap 240 having an extension 66B and bone penetrating member engagement portion 72 also having a unitary construction. The extension 66B has a short truncated conical wall 74B (height of about 1 inch), with ribs 78B, and with a conical angle 76B of about 50 degrees. In this embodiment, there are four ribs 78B equiangularly spaced around the circumference of the truncated conical wall 74B, i.e., spaced at 90 degree intervals. Fewer or additional ribs may be provided and the angular spacing between ribs may be determined as desired. FIG. 17C, moreover, provides an interior view of the cap 240, including projection 54 extending circumferentially around the interior of the bone penetrating member engagement portion 72, from lower rim 50. In this example, the extension 66B extends from a region of the upper wall 48 of the bone penetrating member engagement portion 72, and the region is inward on the upper wall 48 with respect to a region where the peripheral wall 46 meets the upper wall 48.

FIGS. 18A and 18B show an extension 66C and bone penetrating member engagement portion 72 also having a unitary construction. Extension 66C has a tall truncated conical wall 74C (height of about 1.5 inches), without ribs, and with a conical angle 76C of about 30 degrees.

Figure 19A:
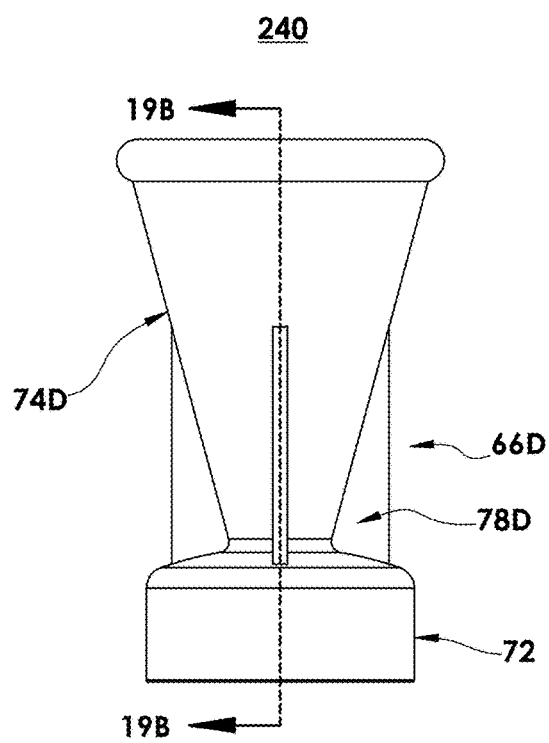
FIG. 19A is a front view of another cap of the bone marrow access apparatus according to the third embodiment.
Figure 19B:
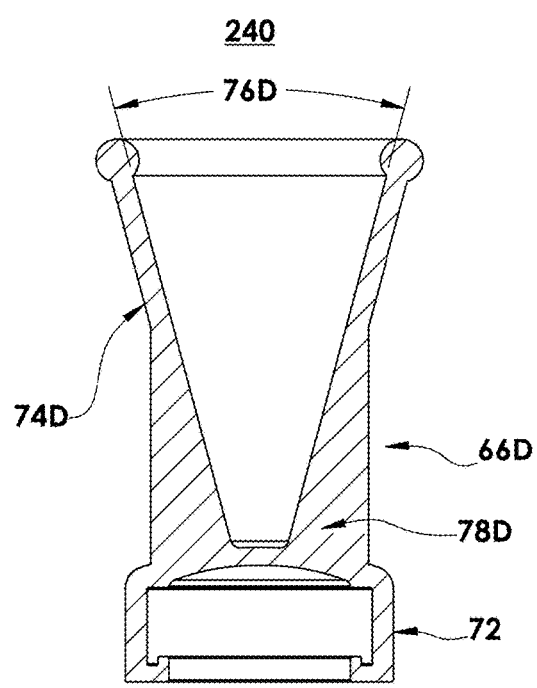
FIG. 19B is a cross-sectional view taken along the line 19B-19B in FIG. 19A.
Figure 20:
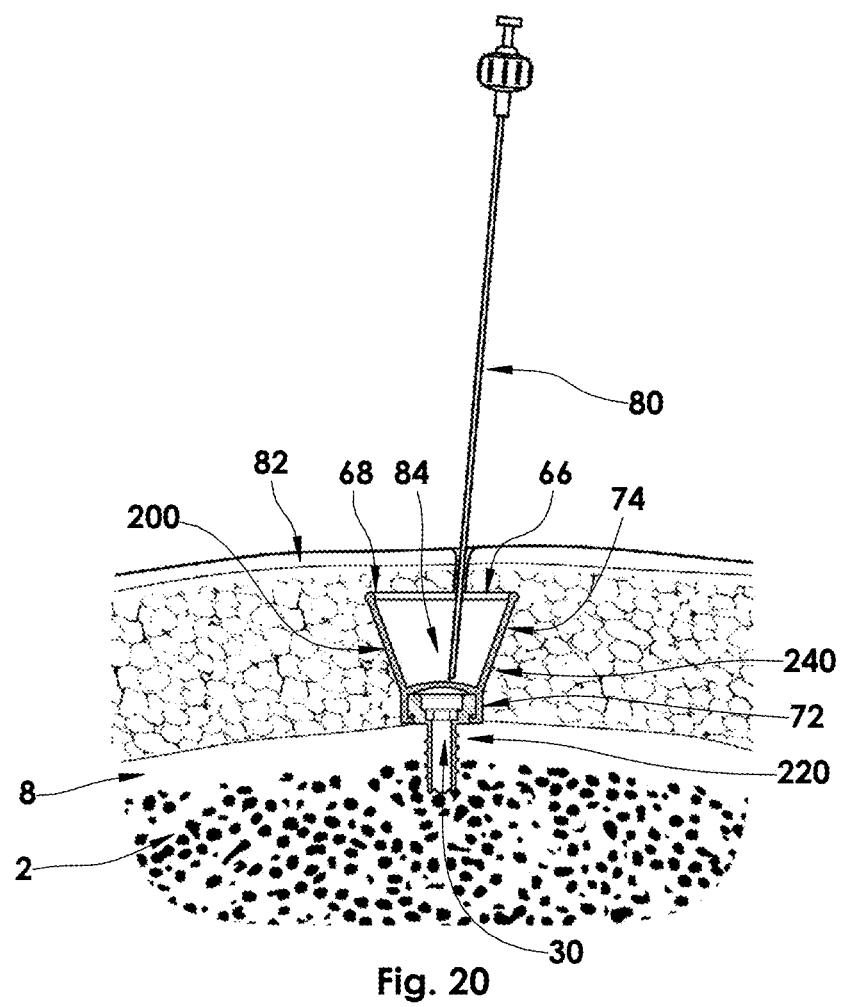
FIG. 20 is a cross-sectional view of the bone marrow access apparatus according to the third embodiment in an installed state and during a sampling needle insertion procedure.
Figure 21:
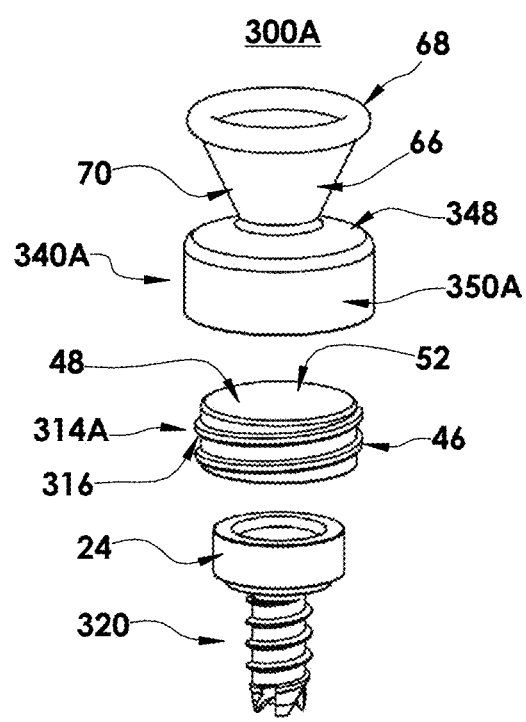
FIG. 21 is a perspective, exploded view of a bone marrow access according to a first example of a fourth embodiment.
Figure 22:
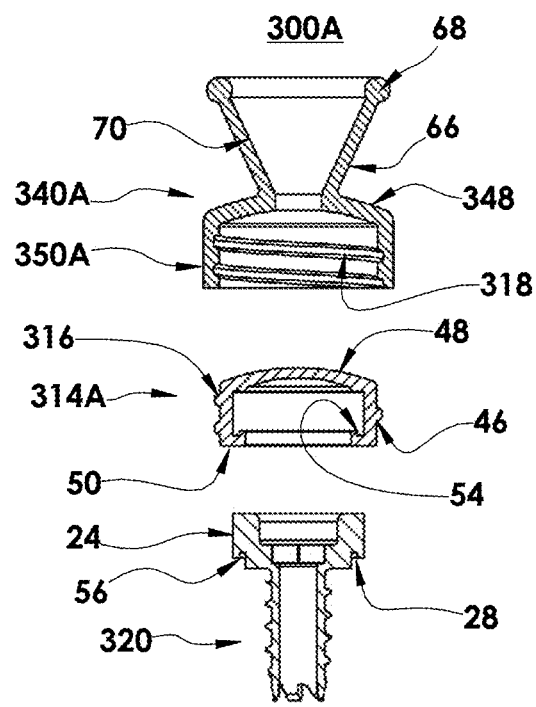
FIG. 22 is a cross-sectional, exploded view of the bone marrow access according to the first example of the fourth embodiment.

FIGS. 19A and 19B show an extension 66D and bone penetrating member engagement portion 72 also having a unitary construction. Extension 66D includes a tall conical wall 74D (height of about 1.5 inches), with four equiangularly spaced ribs 78D, and with a conical angle 76D of about 30 degrees. In this example, the extension 66D extends from a region of the upper wall 48 of the bone penetrating member engagement portion 72, and the region is inward on the upper wall 48 with respect to a region where the peripheral wall 46 meets the upper wall 48.

Installation (and eventual removal) of the bone marrow access apparatus 200 is performed in the same manner as described above with respect to the first embodiment or the second embodiment (depending on whether the cap 240 includes the septum 52 as in the first embodiment or the valve 60 as in the second embodiment). Once the bone marrow access apparatus 200 is installed and the tissue over the apparatus is closed, the extension 66 aids in locating the bone marrow access apparatus under the skin. When using the first and second embodiments without the extension 66, a physician (a surgeon, for example) must press the skin in the generally known area of the bone marrow access apparatus to feel the cap 14 or 140. This may be difficult when the cap 14 or 140 is more than about 2 cm from the skin of the patient. Therefore, by providing the extension 66 (or 66A, 66B, 66C, 66D), locating the cap 240 is significantly easier in that the physician does not locate the cap 240 directly but rather locates the location member 68 which then allows the location of the apparatus of which the location member 68 is a part.

Specifically, each time bone marrow is sampled, a physician would seek the location of the location member 68. This may involve simply looking for a depression (indicating the center of the location member 68) in the known area where the bone marrow access apparatus 200 is located and/or pressing the skin in the known area where the bone marrow access apparatus 200 is located in order to feel for an irregularity such as a crater generated by the location member 68 (see FIG. 15). The physician would then squeeze opposing edges of the location member 68 to form a conduit 84 through which a sampling needle 80 (see FIG. 20), or other instrument, can be passed to the septum 52 (or valve 60). To perform bone marrow sampling, the physician inserts the sampling needle 80 through the skin 82, through the conduit 84 formed by the extension 66, through the septum 52 into the channel 30, and then into the marrow space 2 in the bone 8 (or through the opening 62 of the valve 60, into the channel 30, and then into the marrow space 2 in the bone 8). See FIG. 20.

As an alternative cap-locating procedure, the physician could, after identifying the location of the location member 68, take note of the center of the target area, e.g., the center of the location member 68, and mark the center with a surgical marker. The physician would then place a tip of the sampling needle 80 on the skin mark and push the needle as perpendicularly as possible through the skin 82 to the septum 52 (or valve 60).

The selected sampling needle 80, or other type of instrument, used is one that has a size (gauge) that fits in the channel 30. The penetration depth of the sampling needle 80 or other instrument into the marrow space is also variable by the physician. If a straight sampling needle 80 is selected, the sampling needle 80 may be tilted to sample a fresh area of the marrow space for bone marrow. Additional details about using straight sampling needles and alternative curved sampling needles are described in WO 2018/067525. Regardless of which type of sampling needle is used, after the sampling is completed, the needle 80 is removed from the channel 30 and withdrawn through the septum 52 (or valve 60) and skin. The septum 52 self-heals upon removal of the needle (or the valve 60 closes its opening 62), thereby preventing material flow out of and into the marrow space 2.

Fourth Embodiment

FIGS. 21-34 show bone marrow access apparatuses 300A and 300B in accordance with a fourth embodiment of the invention. FIGS. 21-27 show a bone marrow access apparatus 300A according to a first example of the fourth embodiment, and FIGS. 28-34 show a bone marrow access apparatus according to a second example of the fourth embodiment.

The bone marrow access apparatuses 300A and 300B of the fourth embodiment are similar to the bone marrow access apparatus 200 of the third embodiment, except that the bone marrow access apparatuses 300A and 300B are assembled or formed from three pieces, whereas the bone marrow access apparatus 200 of the third embodiment is assembled or formed from only two pieces.

As shown in FIGS. 21-27, the bone marrow access apparatus 300A includes a bone penetrating member 320, a cap 314A, and an extension cap 340A which includes the extension 66 and location member 68 described above with respect to the third embodiment.

As shown in FIGS. 28-34, the bone marrow access apparatus 300B includes the bone penetrating member 320, a cap 314B, and an extension cap 340B which includes the extension 66 including the location member 68 described above with respect to the third embodiment.

As shown in FIGS. 21-34, the bone penetrating member 320 of the fourth embodiment is identical to the bone penetrating member 220 of the third embodiment. As discussed above with respect to the third embodiment, the bone penetrating member 320 can be identical to the bone penetrating member 12 of the first embodiment. The bone penetrating member 320 can have other configurations, such as the configuration of the bone penetrating member 120 of the second embodiment (with the cap 340A or 340B being appropriately modified to fit the bone penetrating member).

As also shown in FIGS. 21-34, caps 314A and 314B of the fourth embodiment are similar to the cap 14 of the first embodiment, and are attachable to the bone penetrating member 320 in the same way as the cap 14 is attachable to the bone penetrating member 12 of the first embodiment. Thus, for example, the caps 314A and 314B include an upper wall 48 with a septum 52, a peripheral wall 46, and a lower wall or lower rim 50 that is situated in or engages with a step 28 the head portion 24 of the bone penetrating member 320. Moreover, the lower rim 50 has the projection 54 that projects into the groove (recess) 56 of the head portion 24 of the bone penetrating member 320. The caps 314A and 314B can have alternative configurations. For example, the caps 314A and 314B can include the valve 60 and/or the projection 64 of the cap 140 of the second embodiment. The caps 314A and 314B can also omit the projection 54, in a manner similar to the cap 14A of the modification of the first embodiment. Thus, the caps 314A and 314B can have various configurations with various combinations of features of the caps of the bone marrow access apparatuses described herein.

As shown in FIGS. 21-27, the cap 314A of the first example of the fourth embodiment differs from the cap 14 of the first embodiment in that cap 314A has threads 316 projecting from the outside of the peripheral wall 46. The threads 316 can engage with threads 318 formed inside the bottom part of extension cap 340A, to allow cap 340A to be mounted on the cap 314A and bone penetrating member 320 (see FIGS. 23 and 24).

As also shown in FIGS. 21-27, the extension cap 340A includes a cap mating portion 350A with threads 318 formed therein. The cap mating portion 350A has an upper wall 348 which covers the periphery of the upper wall 48 of the cap 314A when the extension cap 340A is mounted on the cap 314A (see FIG. 24). The upper wall 348 does not cover the central part of the upper wall 48 of the cap 314A (see FIG. 24). The extension cap 340A includes the extension 66 projecting from the inner periphery of the upper wall 348. The extension 66 includes the location member 68 at its proximal end, and coupling structure 70 that couples the location member 68 to the upper wall 348.

Figure 23:
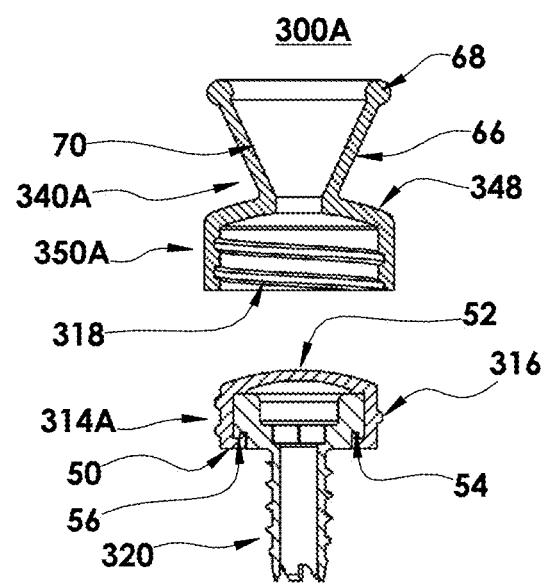
FIG. 23 is a cross-sectional view of the bone marrow access according to the first example of the fourth embodiment in a partially assembled state.
Figure 24:
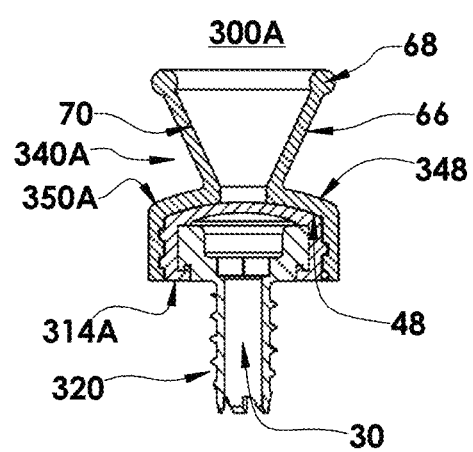
FIG. 24 is a cross-sectional view of the bone marrow access according to the first example of the fourth embodiment in an assembled state.

The bone marrow access apparatus 300A is assembled by first mounting the cap 314A on the head portion 24 of the bone penetrating member 320, and engaging the projection 54 of the cap 314A in the groove 56 of the head portion 24 (FIG. 23). Then, the extension cap 340A is mounted on the cap 314A and the bone penetrating member 320 by screwing the cap mating portion 350A of the extension cap 340A onto the cap 314A, using the threads 318 of the cap mating portion 350A and the threads 316 of the cap 314A (FIG. 24). The extension cap 340A is thereby secured to the cap 314A and the bone penetrating member 320 by engagement of the threads 316 and 318.

As shown in FIGS. 28-34, the cap 314B of the second example of the fourth embodiment differs from the cap 14 of the first embodiment and from the cap 314A of the first example of the fourth embodiment, in that cap 314B has projections 317 projecting from the outside of the peripheral wall 46. The projections 317 are configured to engage with openings 319 in the bottom part of extension cap 340B. The projections 317 are sloped at top (proximal) ends thereof to allow the bottom part of the extension cap 340B to slide over the projections 317. The projections 317 are squared-off at bottom (distal) ends thereof. The projections 317 can thus project into and engage with the openings 319 to prevent the extension cap 340B from sliding off the cap 314B, after the cap extension cap 340B has been mounted on the cap 314B.

As also shown in FIGS. 28-34, the extension cap 340B includes a cap mating portion 350B with the openings 319 formed therein. The cap mating portion 350B has an upper wall 348 which covers the periphery of the upper wall 48 of the cap 314B when the extension cap 340B is mounted on the cap 314B (see FIG. 31). The upper wall 348 does not cover the central part of the upper wall 48 of the cap 314B (see FIG. 31). The extension cap 340B includes the extension 66 projecting from the inner periphery of the upper wall 348. The extension 66 includes the location member 68 at its proximal end, and coupling structure 70 that couples the location member 68 to the upper wall 348.

Figure 30:
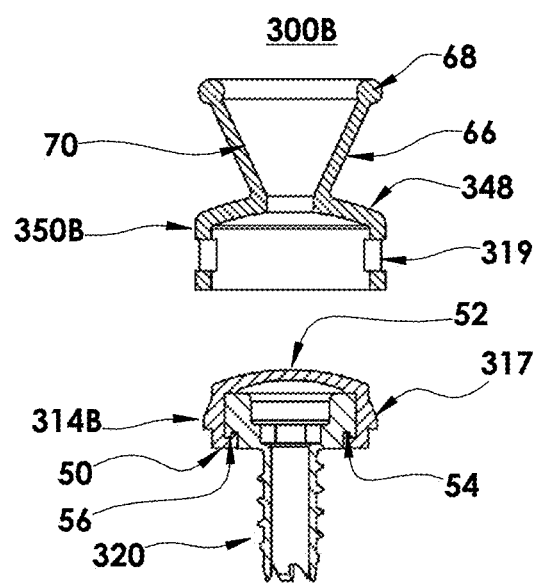
FIG. 30 is a cross-sectional view of the bone marrow access according to the second example of the fourth embodiment in a partially assembled state.
Figure 31:
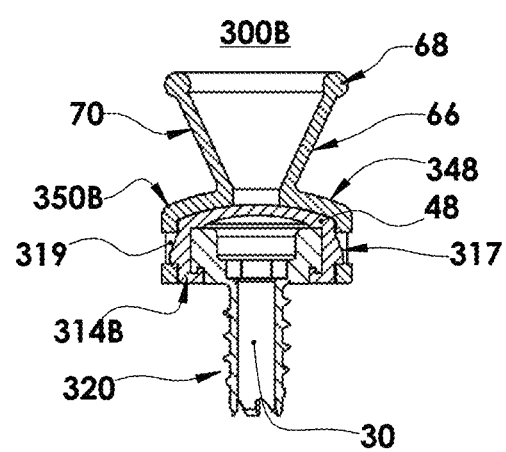
FIG. 31 is a cross-sectional view of the bone marrow access according to the second example of the fourth embodiment in an assembled state.

The bone marrow access apparatus 300B is assembled by first mounting the cap 314B on the head portion 24 of the bone penetrating member 320, and engaging the projection 54 of the cap 314 in the groove 56 of the head portion 24 (FIG. 30). Then, the extension cap 340B is mounted on the cap 314B and the bone penetrating member 320 by sliding the cap mating portion 350B over the cap 314B, until the projections 317 of the cap 314B engage in the openings 319 of the cap mating portion 350B (FIG. 31). The extension cap 340B is thereby secured to the cap 314B and the bone penetrating member 320 by engagement of the projections 317 and openings 319.

The extension 66 of extension cap 340A and extension cap 340B, including the coupling structure 70 and the location member 68, can have various configurations, including all of the configurations described above with respect to extensions 66, 66A, 66B, 66C, and 66D of the third embodiment. For example only, the extension 66 of the extension cap 340A and extension cap 340B can include ribs as described above with respect to extensions 66B and 66D of the third embodiment, and the extension 66 of extension cap 340A and extension cap 340B can have various conical angles and various heights as described above with respect to extensions 66, 66A, 66B, 66C, and 66D of the third embodiment. The material or materials used to form extension cap 340A and extension cap 340B can be the same as those described above for forming the extension 66. Considerations relating to hardness of the extension 66 of the extension cap 340A and extension cap 340B are the same as or similar to those described above with respect to the extensions 66, 66A, 66B, 66C, and 66D of the third embodiment.

The structure of the fourth embodiment may be delivered to a purchaser or end user (e.g., a physician) as a kit including the bone penetrating member 320 and cap 314A or 314B (generally, but not necessarily, with bone penetrating member 320 and cap 314A or 314B preassembled) and the extension cap 340A or 340B.

Figure 25:
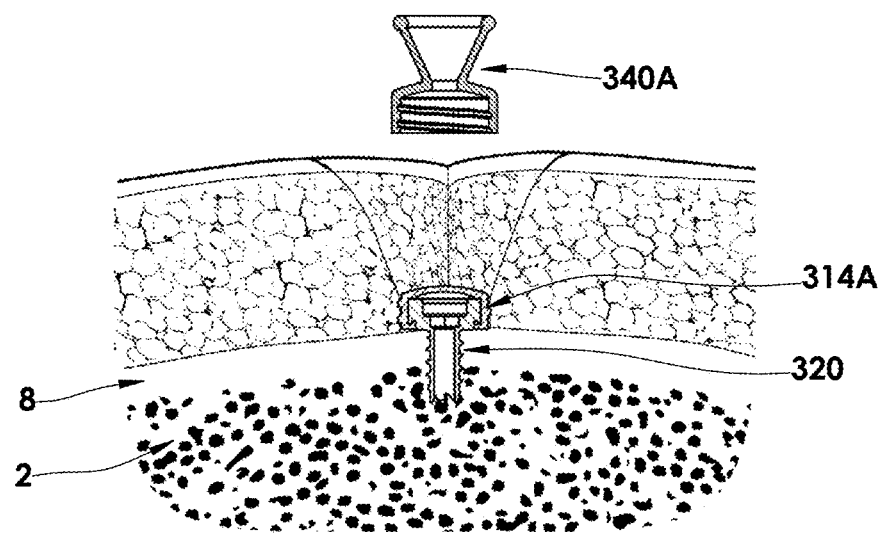
FIG. 25 is a cross-sectional view of the bone marrow access apparatus according to the first example of the fourth embodiment during an installation stage.
Figure 26:
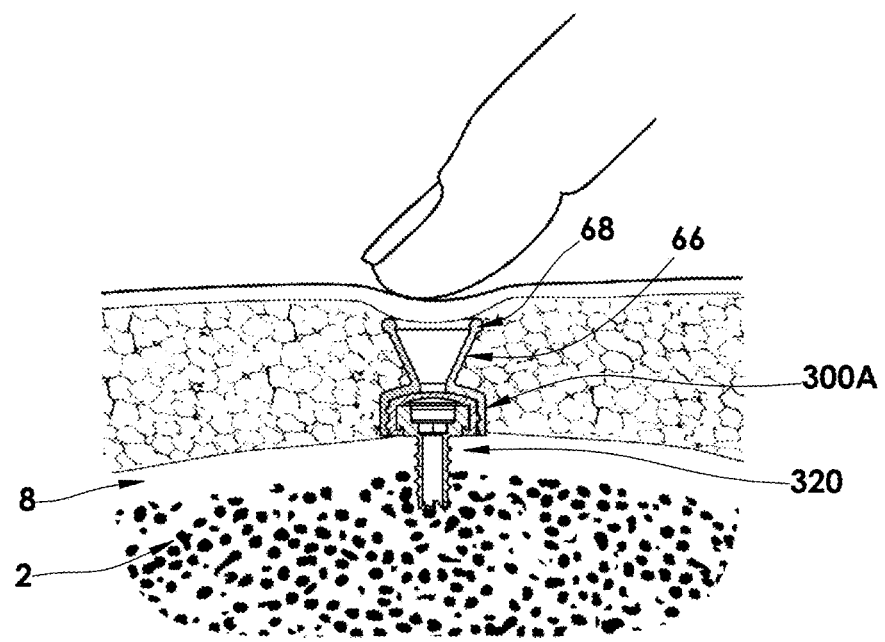
FIG. 26 is a cross-sectional view of the bone marrow access apparatus according to the first example of the fourth embodiment in an installed state and during a locating procedure.
Figure 27:
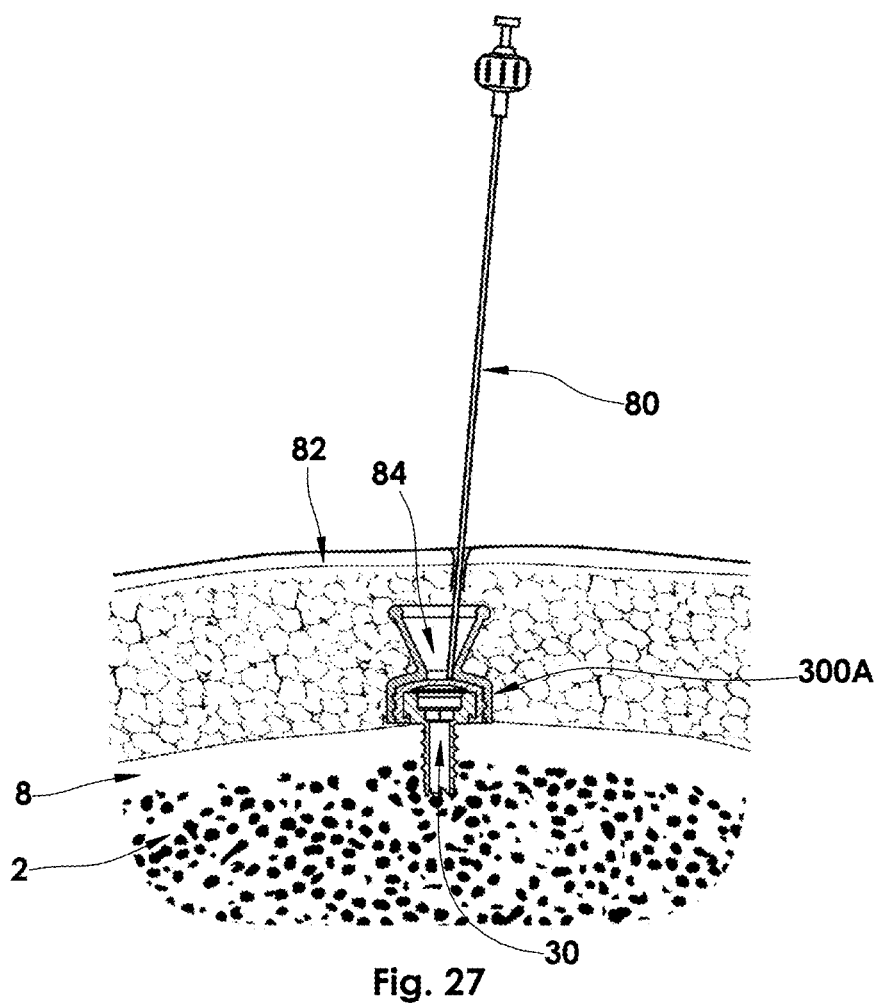
FIG. 27 is a cross-sectional view of the bone marrow access apparatus according to the first example of the fourth embodiment during in an installed state and during a sampling needle insertion procedure.
Figure 28:
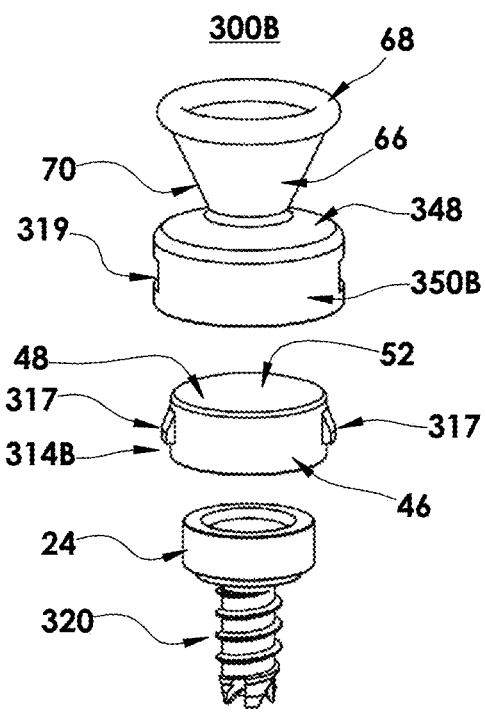
FIG. 28 is a perspective, exploded view of a bone marrow access according to a second example of a fourth embodiment.
Figure 29:
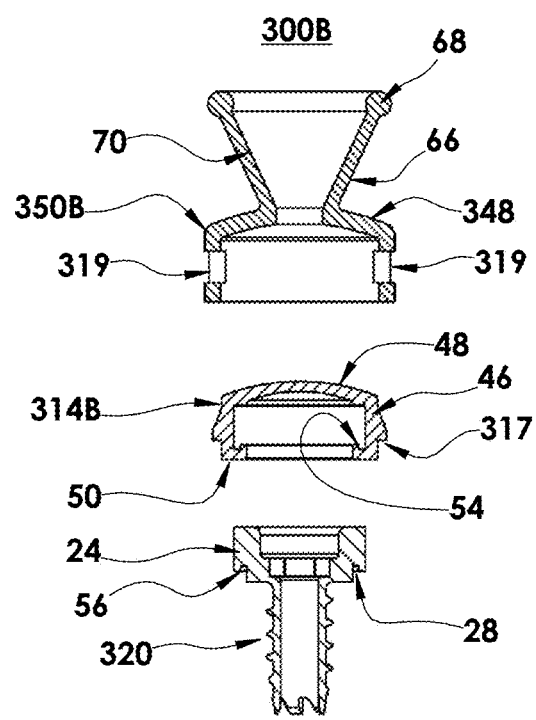
FIG. 29 is a cross-sectional, exploded view of the bone marrow access according to the second example of the fourth embodiment.
Figure 32:
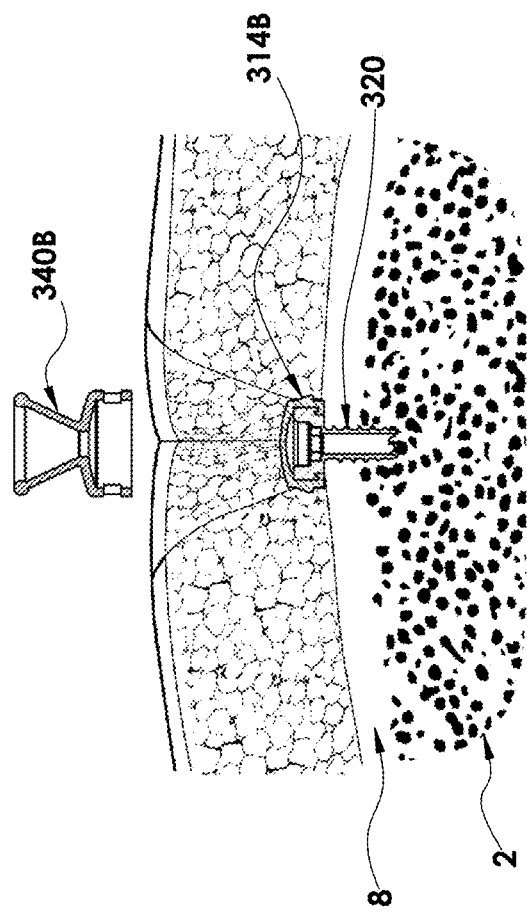
FIG. 32 is a cross-sectional view of the bone marrow access apparatus according to the second example of the fourth embodiment during an installation stage.
Figure 33:
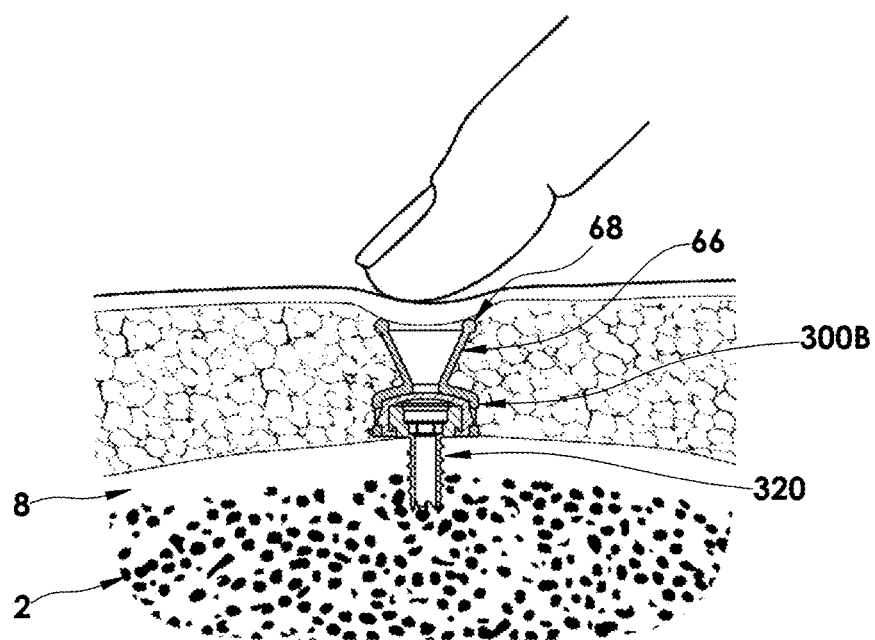
FIG. 33 is a cross-sectional view of the bone marrow access apparatus according to the second example of the fourth embodiment in an installed state and during a locating procedure.
Figure 34:
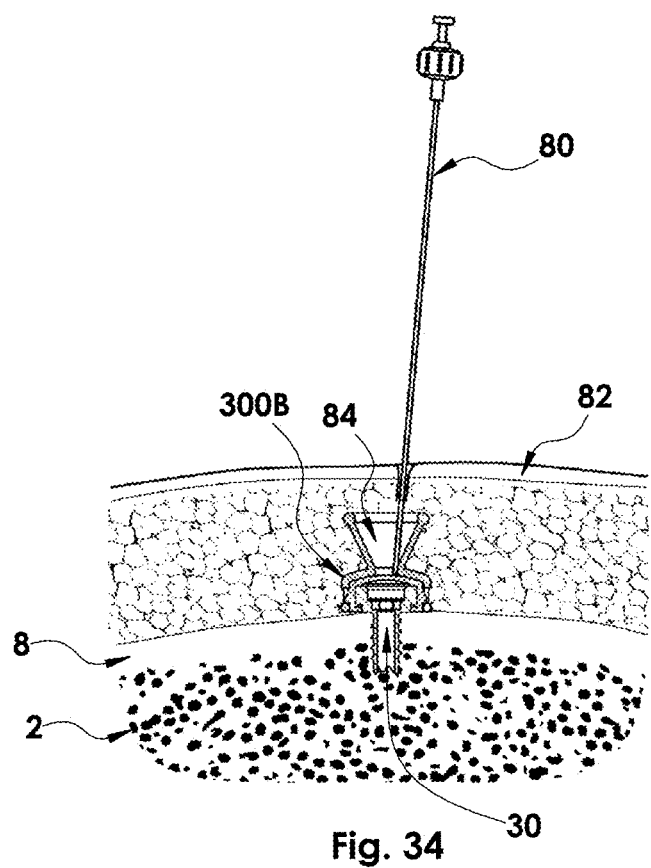
FIG. 34 is a cross-sectional view of the bone marrow access apparatus according to the second example of the fourth embodiment during in an installed state and during a sampling needle insertion procedure.
Figure 35:
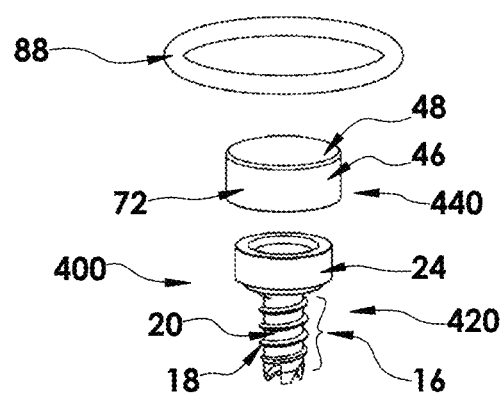
FIG. 35 is a perspective, exploded view of a bone marrow access according to a fifth embodiment.
Figure 36:
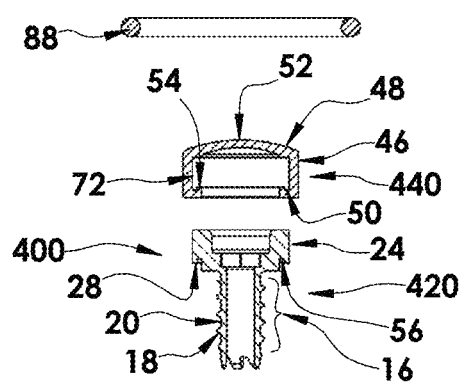
FIG. 36 is a cross-sectional, exploded view of the bone marrow access according to the fifth embodiment.
Figure 37:
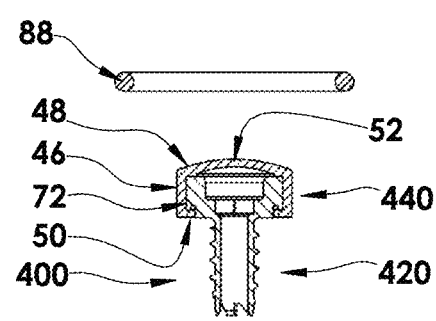
FIG. 37 is a cross-sectional view of the bone marrow access according to the fifth embodiment in an assembled state.
Figure 38:
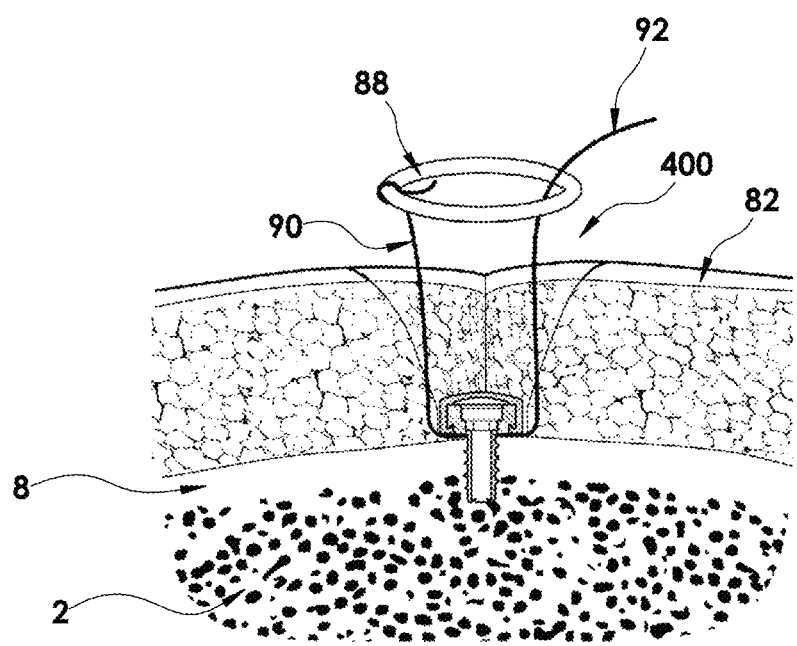
FIG. 38 is a cross-sectional view of the bone marrow access apparatus according to the fifth embodiment during an installation stage.

The first stage of installation of the bone marrow access apparatus 300A or 300B is performed in substantially the same manner as described above with respect to the first embodiment or the second embodiment (depending on whether the cap 314A or 314B includes the septum 52 as in the first embodiment or the valve 60 as in the second embodiment). That is, the assembly of the bone penetrating member 320 with the cap 314A (refer to FIGS. 23 and 25), or the assembly of the bone penetrating member 320 with the cap 314B (refer to FIGS. 30 and 32) is first installed in the bone in substantially the same manner as described above with respect to the first embodiment or the second embodiment (FIGS. 25 and 32). The installation of the bone marrow access apparatus 300A or 300B differs from the installation described in the first and second embodiments by including a second stage. In the second stage, after the assembly of the bone penetrating member 320 and cap 314A or 314B is installed in the bone 8 (FIGS. 25 and 32), the extension cap 340A is installed on cap 314A (see FIGS. 24, 26, and 27), or the extension cap 340B is installed on the cap 314B (see FIGS. 31, 33, and 34). Eventual removal of the bone marrow access apparatus 300A or 300B can be performed as described above with respect to the first or second embodiments.

It is also envisioned that the engagement of the bone penetrating member 320, cap 314A, and extension cap 340A, or the engagement of the bone penetrating member 320, cap 314B, and extension cap 340B, can be performed at a manufacturing stage, before supplying the bone marrow access apparatus 300A or 300B to a purchaser or end user (e.g., a physician). Accordingly, the bone marrow access apparatus 300A or 300B can be supplied to the user as a single, integrated unit. In this case, installation of the bone marrow access apparatus 300A or 300B would be performed in the same manner as in the third embodiment described above.

In the same manner as described above with respect to the third embodiment, once the bone marrow access apparatus 300A or 300B is installed and the tissue over the apparatus is closed (FIGS. 26 and 33), the extension 66 aids in locating the bone marrow access apparatus under the skin. Specifically, each time bone marrow is sampled, a physician would seek the location of the location member 68. This may involve simply looking for a depression (indicating the center of the location member 68) in the known area where the bone marrow access apparatus 300A or 300B is located and/or pressing the skin in the known area where the bone marrow access apparatus 300A or 300B is located in order to feel for an irregularity such as a crater generated by the location member 68 (see FIGS. 26 and 33). The physician would then squeeze opposing edges of the location member 68 to form a conduit 84 through which a sampling needle 80

(FIGS. 27 and 34), or other instrument, can be passed to the septum 52 (or valve 60). To perform bone marrow sampling, the physician inserts the sampling needle 80 through the skin 82, through the conduit 84 formed by the extension 66, through the septum 52 into the channel 30, and then into the marrow space 2 in the bone 8 (or through the opening 62 of the valve 60, into the channel 30, and then into the marrow space 2 in the bone 8). See FIGS. 27 and 34.

As an alternative cap-locating procedure, the physician could, after identifying the location of the location member 68, take note of the center of the target area, e.g., the center of the location member 68, and mark the center with a surgical marker. The physician would then place a tip of the sampling needle 80 on the skin mark and push the needle 80 as perpendicularly as possible through the skin 82 to the septum 52 (or valve 60).

The selected sampling needle 80, or other type of instrument, used is one that has a size (gauge) that fits in the channel 30. The penetration depth of the sampling needle 80 or other instrument into the marrow space is also variable by the physician. If a straight sampling needle 80 is selected, the sampling needle 80 may be tilted to sample a fresh area of the marrow space for bone marrow. Additional details about using straight sampling needles and alternative curved sampling needles are described in WO 2018/067525. Regardless of which type of sampling needle is used, after the sampling is completed, the needle 80 is removed from the channel 30 and withdrawn through the septum 52 (or valve 60) and skin. The septum 52 self-heals upon removal of the needle (or the valve 60 closes its opening 62), thereby preventing material flow out of and into the marrow space 2.

Fifth Embodiment

FIGS. 35-43 show a bone marrow access apparatus 400 in accordance with a fifth embodiment of the invention. As shown in FIGS. 35-43, the bone marrow access apparatus 400 includes a bone penetrating member 420, a cap 440, a ring 88, and a coupling structure 90.

The bone penetrating member 420 is identical to the bone penetrating member 220 of the third embodiment and the bone penetrating member 320 of the fourth embodiment. As discussed above with respect to the third and fourth embodiments, the bone penetrating member 420 can thus be identical to the bone penetrating member 12 of the first embodiment. The bone penetrating member 420 can have other configurations, such as the configuration of the bone penetrating member 120 of the second embodiment (with the cap 440 being appropriately modified to fit the bone penetrating member 420).

The cap 440 is identical to the cap 14 of the first embodiment, but can alternatively be identical to the cap 140 of the second embodiment. The cap 440 can also have other configurations, including configurations which combine features of the first embodiment (such as the projection 54) with features of the second embodiment (such as the valve 60 and/or projection 64).

The ring 88 serves as a location member in a similar manner to the location member 68 of the third embodiment. That is, the ring 88 serves as a location member that allows the bone penetrating member 420 and cap 440 to be easily located by tactile and/or visual location. Unlike the location member 68 of the third and fourth embodiments, the ring 88 of the fifth embodiment is a separate component from (not integrated with) the cap 440. As shown, the ring 88 is an O-ring, but other shapes of a ring may be used. The ring 88 may be made of silicone.

The coupling structure 90 (see FIGS. 38, 39, and 41) couples the ring 88 to the bone penetrating member 420 or cap 440 to position the ring 88 at a distance from the upper surface of the bone penetrating member 420 and cap 440. In the illustrated embodiment, the coupling structure 90 is threaded through the cap 440 and through or around the ring 88. The coupling structure 90 can be a filament 92, which may be a suture (or another material used in closing a wound), thread, gut, wire, or any slender or threadlike structure, that is able to be threaded through the peripheral wall 46, the upper wall 48, and/or the lower rim 50 as well as through or around the ring 88.

The structure of the fifth embodiment may be delivered to a purchaser or end user as a kit including the bone penetrating member 420 and cap 440 (generally, but not necessarily, with bone penetrating member 420 and cap 440 preassembled) and the ring 88. The coupling structure 90 (filament 92) may optionally be included in such a kit.

Installation (and eventual removal) of the bone marrow access apparatus 400 is performed in substantially the same manner as described above with respect to the first embodiment or the second embodiment (depending on whether the cap 440 includes the septum 52 as in the first embodiment or the valve 60 as in the second embodiment). The installation differs in that after the assembly of the bone penetrating member 420 and the cap 440 is installed in the bone 8 (see FIG. 38), tissue is dissected to fit the ring 88 right under the subcutaneous layer. The height of the ring 88 can be adjusted by tying the ring 88 to the cap 440 at a desired length (see FIG. 38). The ring 88 may be below the skin 82 and above the tissue (see FIG. 39). After the skin is closed up, an irregularity in the skin will be visible and/or palpable, which irregularity may be either a raised ring of skin or unnatural depression (see FIG. 40).

Figure 39:
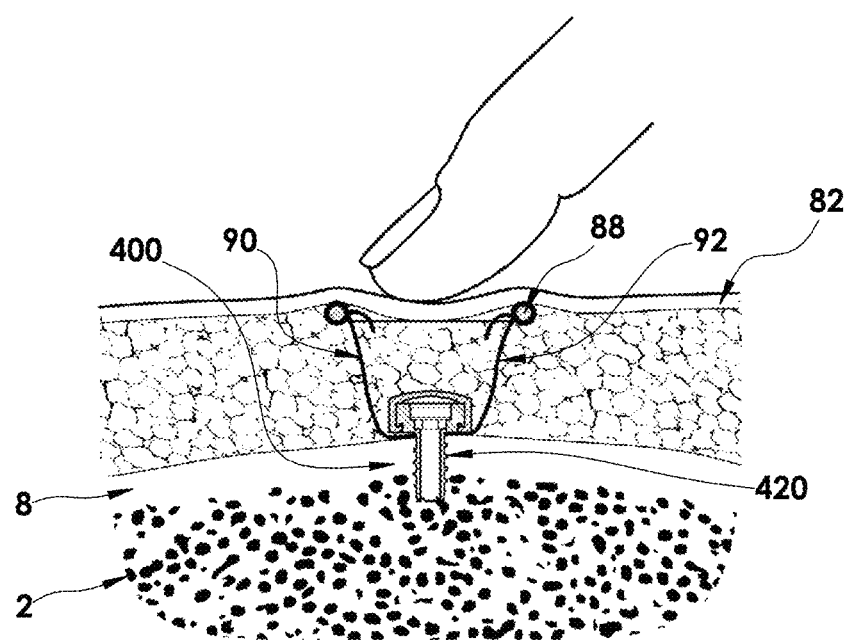
FIG. 39 is a cross-sectional view of the bone marrow access apparatus according to the fifth embodiment in an installed state and during a locating procedure.
Figure 40:
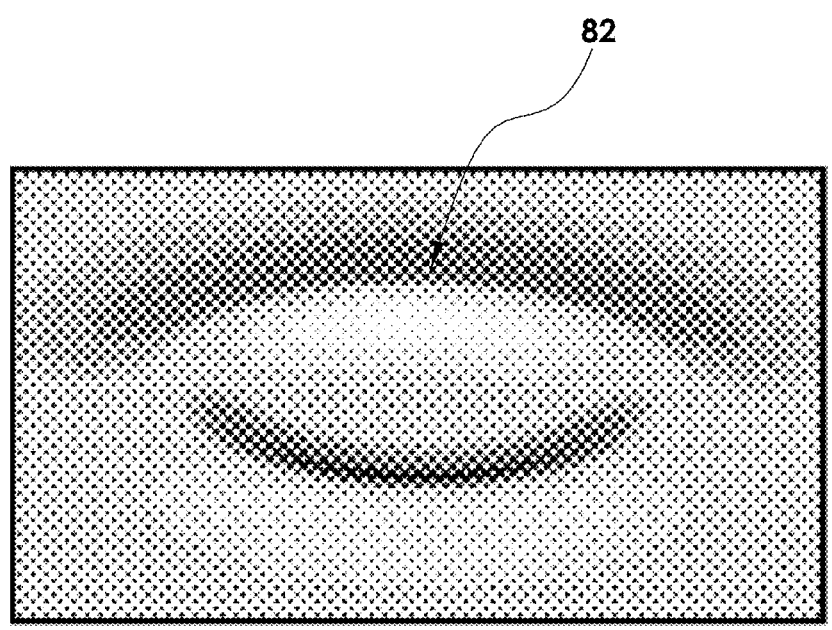
FIG. 40 is a view of skin showing the effect of the installation of the bone marrow access apparatus according to the fifth embodiment.
Figure 41:
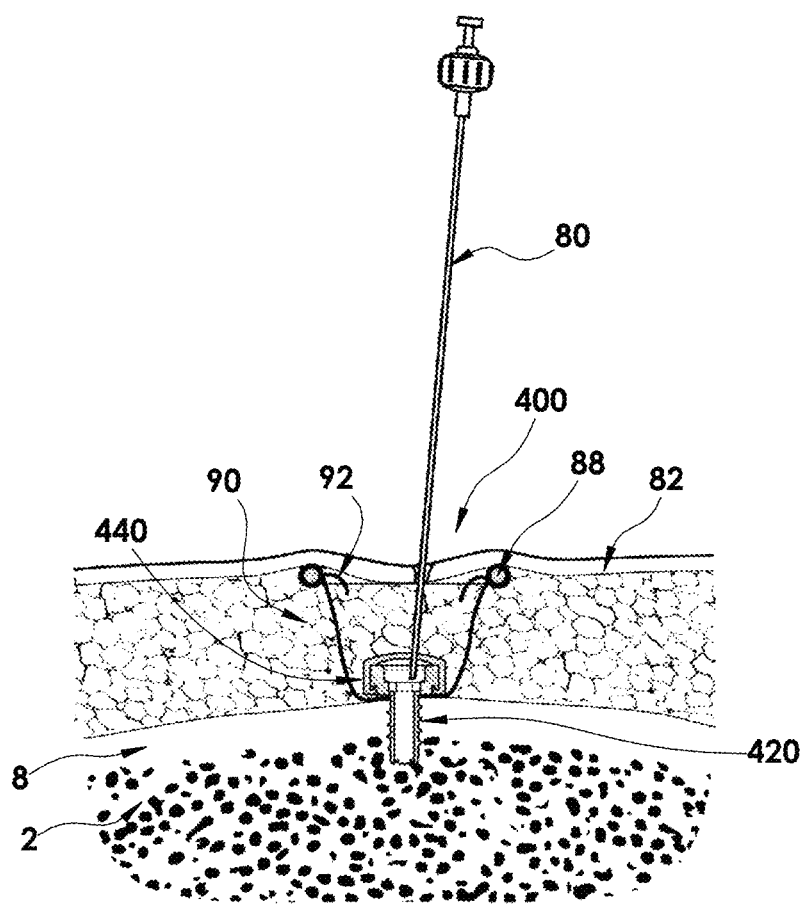
FIG. 41 is a cross-sectional view of the bone marrow access apparatus according to the fifth embodiment in an installed state and during a sampling needle insertion procedure.

Each time bone marrow is sought to be sampled, a physician would feel or look for the irregularity in the appearance of the skin 82 (see FIG. 40), and could press down on the skin 82 and feel for a crater in the middle of the skin 82 caused by the ring 88 (see FIG. 39). The physician would note the center of the ring 88, marking the skin 82 at that location with a surgical marker if necessary. The physician would then place a tip of the sampling needle 80 at the center of the ring 88 or on the skin mark and push the needle as perpendicularly as possible through the skin 82 to the septum 52 (or valve 60) (see FIG. 41).

The ring 88 may also be used in conjunction with a bone penetrating member used without a cap. In this case, the ring 88 could be secured to the bone penetrating member by, for example looping the filament 92 underneath the step 28 and around the bone penetrating member.

Sixth Embodiment

The sixth embodiment, illustrated in FIGS. 42-46, provides a technique for locating a bone marrow access apparatus, which is especially useful for a bone marrow access that does not include the extension 66 of the third or fourth embodiments or the ring 88 of the fifth embodiment. For example, the technique of the sixth embodiment may be used with the bone marrow access apparatuses 10 and 100 of the first and second embodiments, or with a bone marrow access apparatus that is a bone penetrating member without a cap. The technique can also be used with other bone marrow access apparatuses, such as those disclosed in WO 2018067525. For convenience, the following description refers to the bone marrow access apparatus 10.

Figure 42:
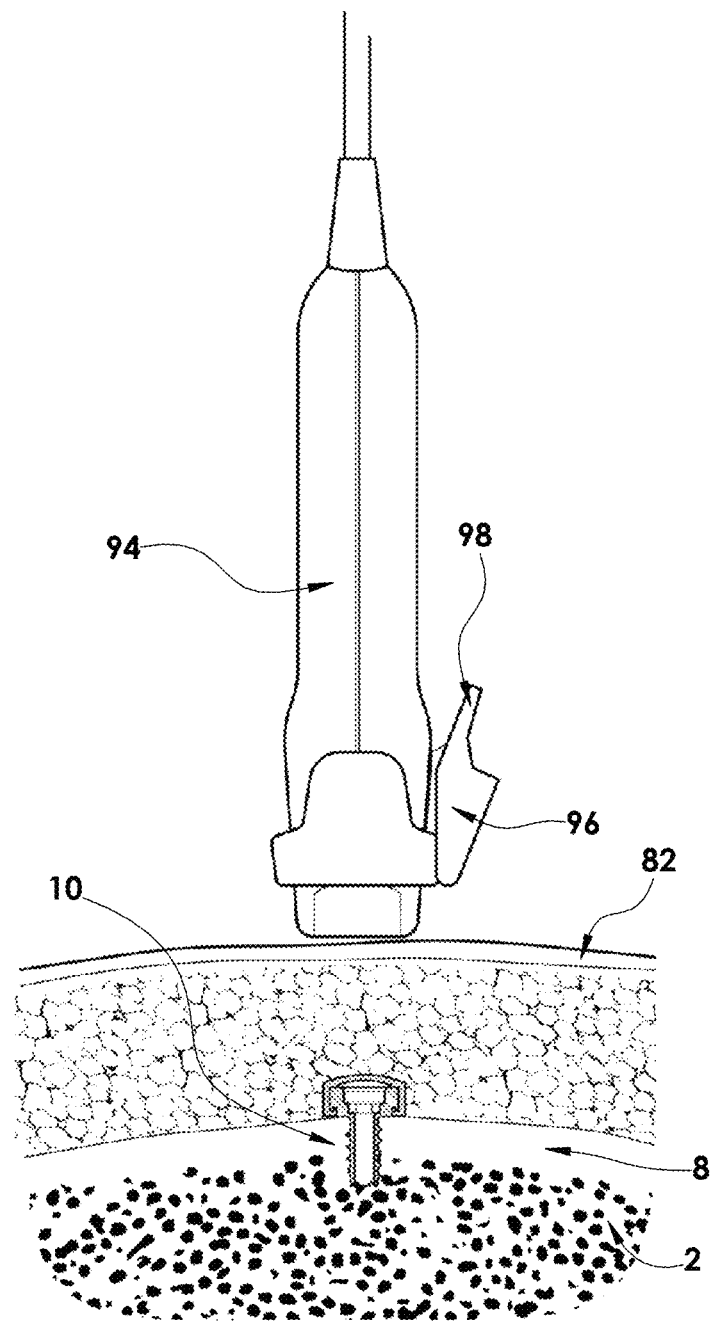
FIG. 42 is a view showing an ultrasound probe with a guide clip used to locate a bone marrow access apparatus.

As shown in FIG. 42, an ultrasound probe 94 is provided to which a clip 96 is attached. The clip 96 has a tool guide 98. The attachment position of the clip 96 to the ultrasound probe 94 is calibrated to provide an accurate track when the bone marrow access apparatus 10 is viewed in the appropriate shape in an ultrasound image on a monitor (see FIG. 43).

Figure 43:
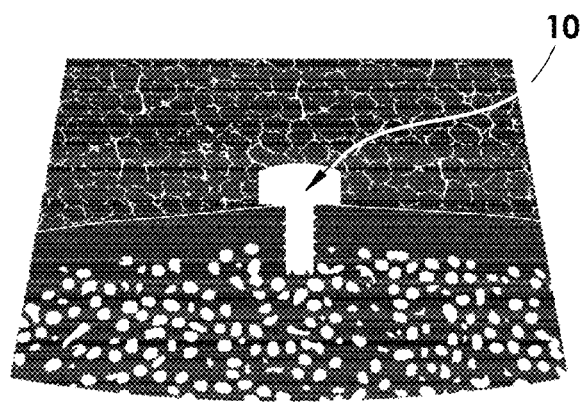
FIG. 43 is a view representing an ultrasound image showing a bone marrow access apparatus.

To locate the bone marrow access apparatus 10, a physician moves the ultrasound probe 94 on the skin 82 over general area in which the bone marrow access apparatus 10 is expected to be located until it appears as shown in FIG. 43. Since the bone marrow access apparatus 10, or at least part of the bone marrow access apparatus 10 (the cap 14 and/or the bone penetrating member 12), is made of material(s) such as silicones, plastics and/or metal that appear different from tissue and bone during ultrasonic imaging, the ultrasound image will reveal the bone marrow access apparatus 10 among the surrounding tissue and bone.

Figure 44:
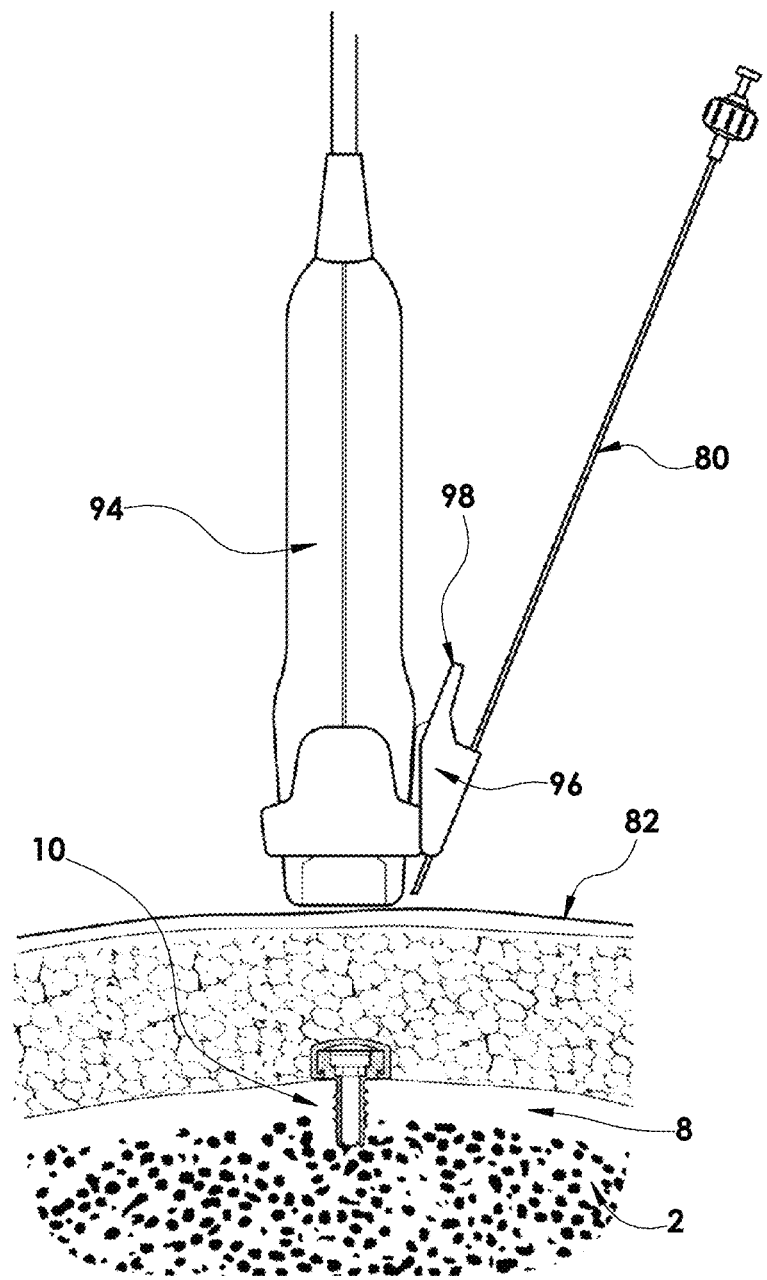
FIG. 44 is a view showing an ultrasound probe with a sampling needle.
Figure 45:
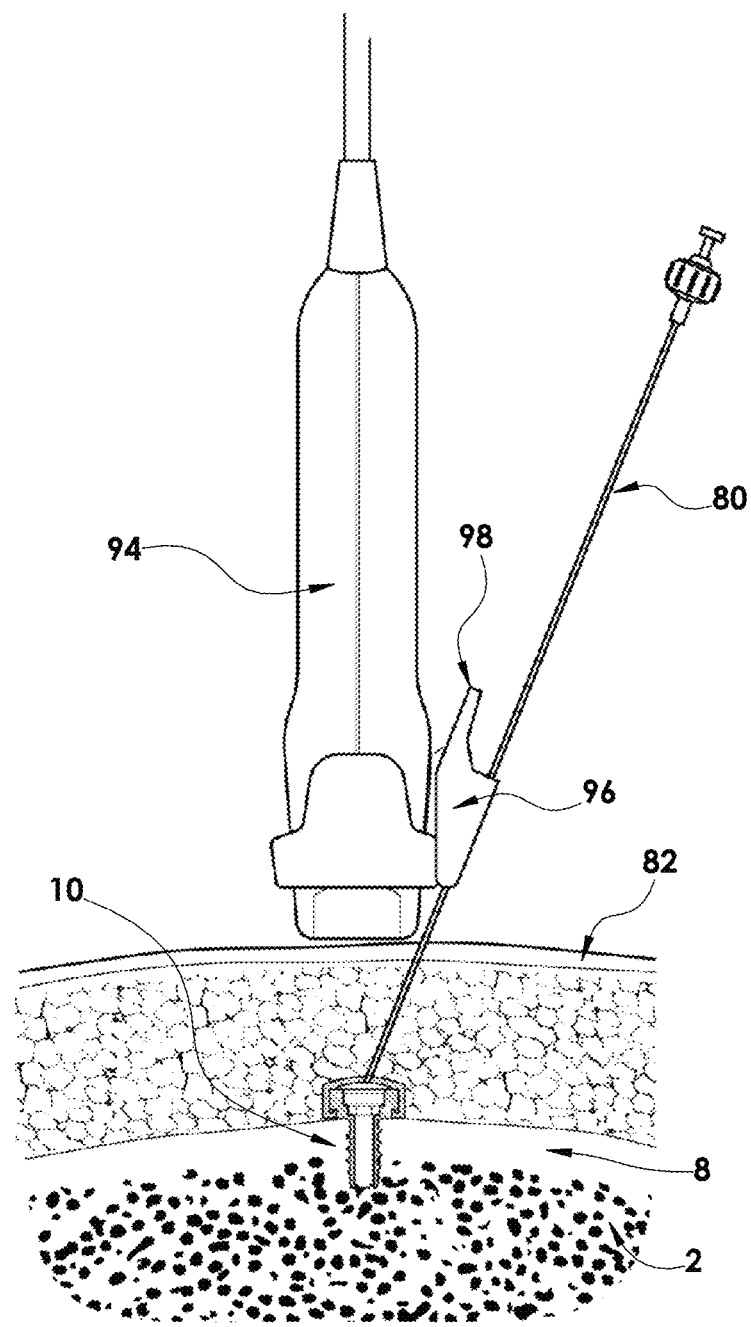
FIG. 45 is a view showing an ultrasound probe with a sampling needle during a bone marrow sampling procedure.
Figure 46:
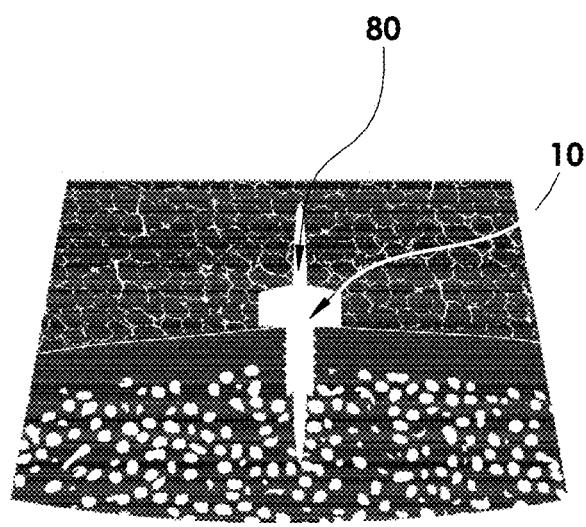
FIG. 46 is a view representing an ultrasound image showing a bone marrow access apparatus during a bone marrow sampling procedure.

For bone marrow sampling, the physician inserts an operative end of a sampling device, e.g., the tip of the sampling needle 80, into the tool guide 98 before or after moving the ultrasound probe 94 to locate the bone marrow access apparatus (see FIG. 44). The physician then holds the tool guide 98 in place and pushes the tip of sampling needle 80 toward the bone marrow access apparatus 10 until the physician senses tactile feedback from contact with the cap 14 (see FIG. 45). At this time, the ultrasound image should appear as shown in FIG. 46. The physician then pushes the tip of sampling needle 80 through the bone marrow access apparatus 10 and into the bone marrow space 2 to perform the bone marrow sampling. This locating technique (like other locating techniques and structures described in the present application) could also be used to locate the bone marrow access apparatus 10 for the purpose of inserting a delivery device to deliver fluid, drugs, or other material to the bone marrow space 2.

Seventh Embodiment

The seventh embodiment, illustrated in FIGS. 47-53, provides another technique for locating a bone marrow access apparatus, which again is especially useful for a bone marrow access that does not include the extension 66 of the third or fourth embodiments or the ring 88 of the fifth embodiment. For example, the technique of the seventh embodiment may be used with the bone marrow access apparatuses 10 and 100 of the first and second embodiments, or with a bone marrow access apparatus that is a bone penetrating member without a cap. The technique can also be used with other bone marrow access apparatuses, such as those disclosed in WO 2018/067525. For convenience, the following description refers to the bone marrow access apparatus 10.

Figure 47:
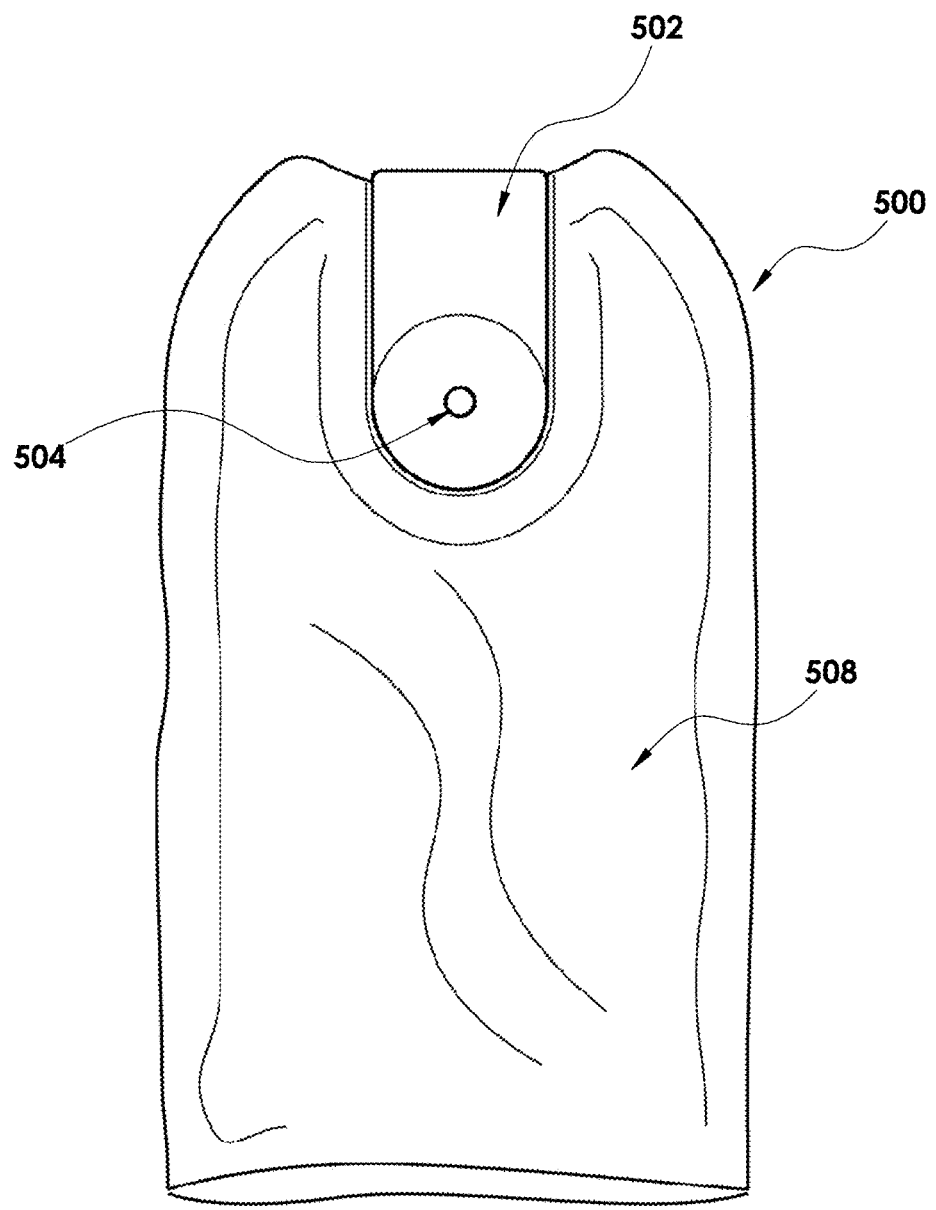
FIG. 47 is a view showing an illuminator used to locate a bone marrow access apparatus, with the illuminator inside a bag.
Figure 48:
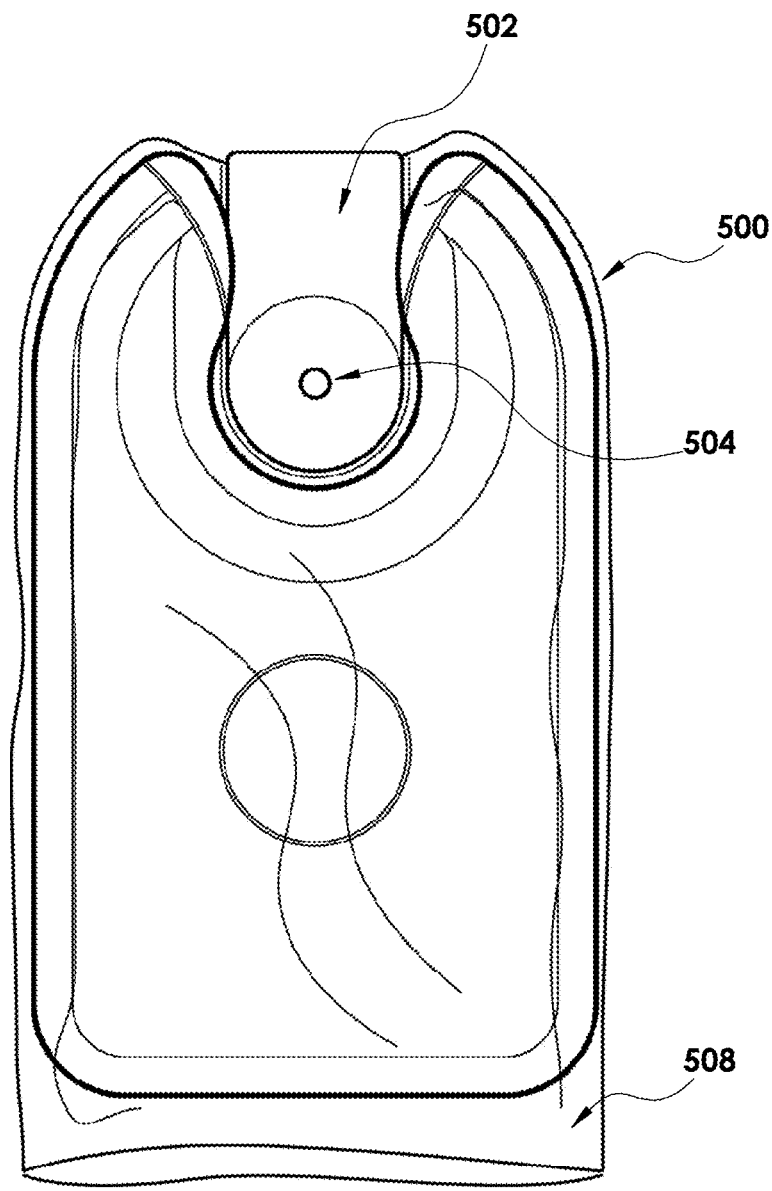
FIG. 48 is a view showing the illuminator used to locate a bone marrow access apparatus, with the bag shown transparently to show the illuminator.
Figure 49:
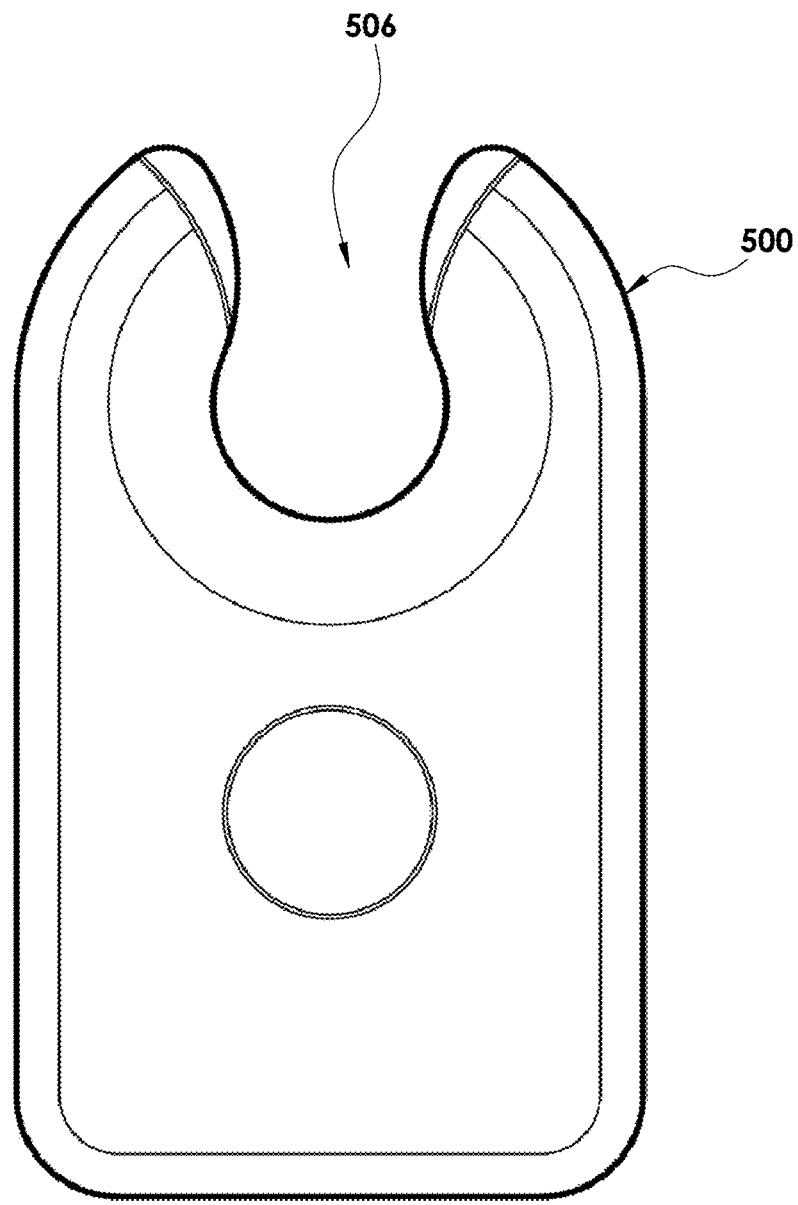
FIG. 49 is a top view of the illuminator used to locate a bone marrow access apparatus, removed from the bag and without a sampling needle clip.

As shown in FIGS. 47-53, a vein illuminator 500 is provided to target the bone marrow access apparatus 10 and ensure that a sampling needle 80 tracks to the bone marrow access apparatus 10. The illuminator 500 has an aperture 506 (FIG. 49), in which a disposable U-shaped clip 502 with one or more centering holes 504 is placed. A bag 508, e.g., a polybag, can be placed around the illuminator 500 to provide a sterile barrier between the illuminator 500 and the patient (see FIGS. 47 and 48). FIG. 47 shows the polybag as being opaque or translucent. FIG. 48 shows the bag as transparent. A polybag, often referred to as a plastic bag or pouch, is considered herein to be a type of container made of thin, flexible, plastic film, nonwoven fabric, or plastic textile, often disposable.

Figure 50:
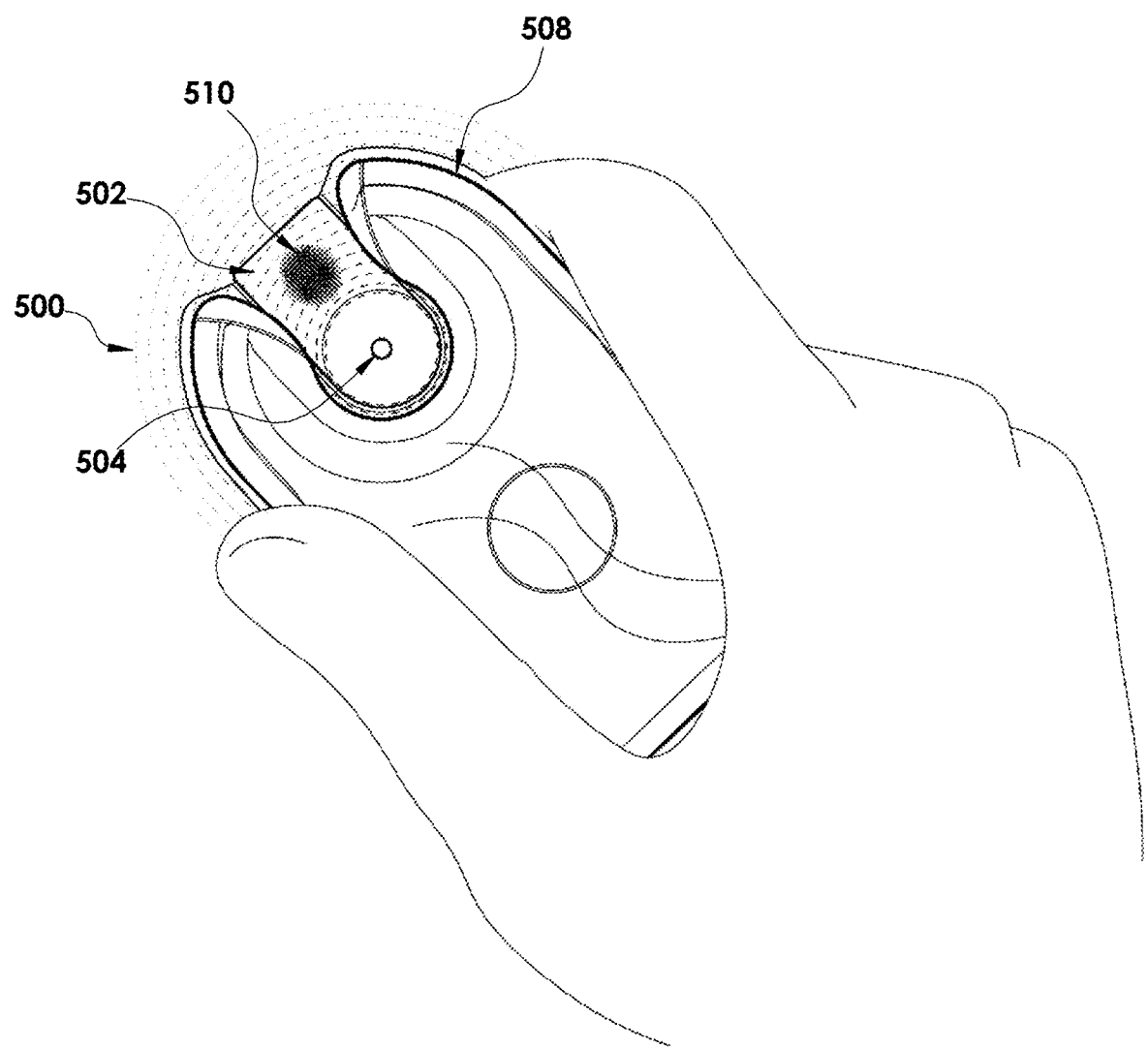
FIG. 50 is a view showing the illuminator during a bone marrow access apparatus locating procedure.

To locate bone marrow access apparatus 10, the bag 508 is placed over the illuminator 500 and the clip 502 is then inserted into the aperture 506 of the illuminator 500 (see FIGS. 47-51). A physician activates the illuminator 500 to turn the LED lights on and places the illuminator 500 on the skin 82 in the general area where the bone marrow access apparatus 10 is known to be present (contact between the skin and the bag 508 around the illuminator 500 is considered here to constitute contact between the illuminator 500 and the skin 82). See FIGS. 50-52 (for clarity, the bag 408 is omitted from FIG. 52 and space is shown between illuminator 500 and skin 82). The illuminator 500 is then moved along the skin 82, preferably maintaining it in contact with the skin 82. Under illumination by the vein illuminator 500, the bone marrow access apparatus 10 appears visually different, e.g., as a darker colored circle 510, as shown in FIG. 50. This visual difference is not limited to a difference in color or color variations. Other techniques to provide for a visual differentiation between the bone marrow access apparatus 10 and surrounding region may be used in the invention.

Figure 51:
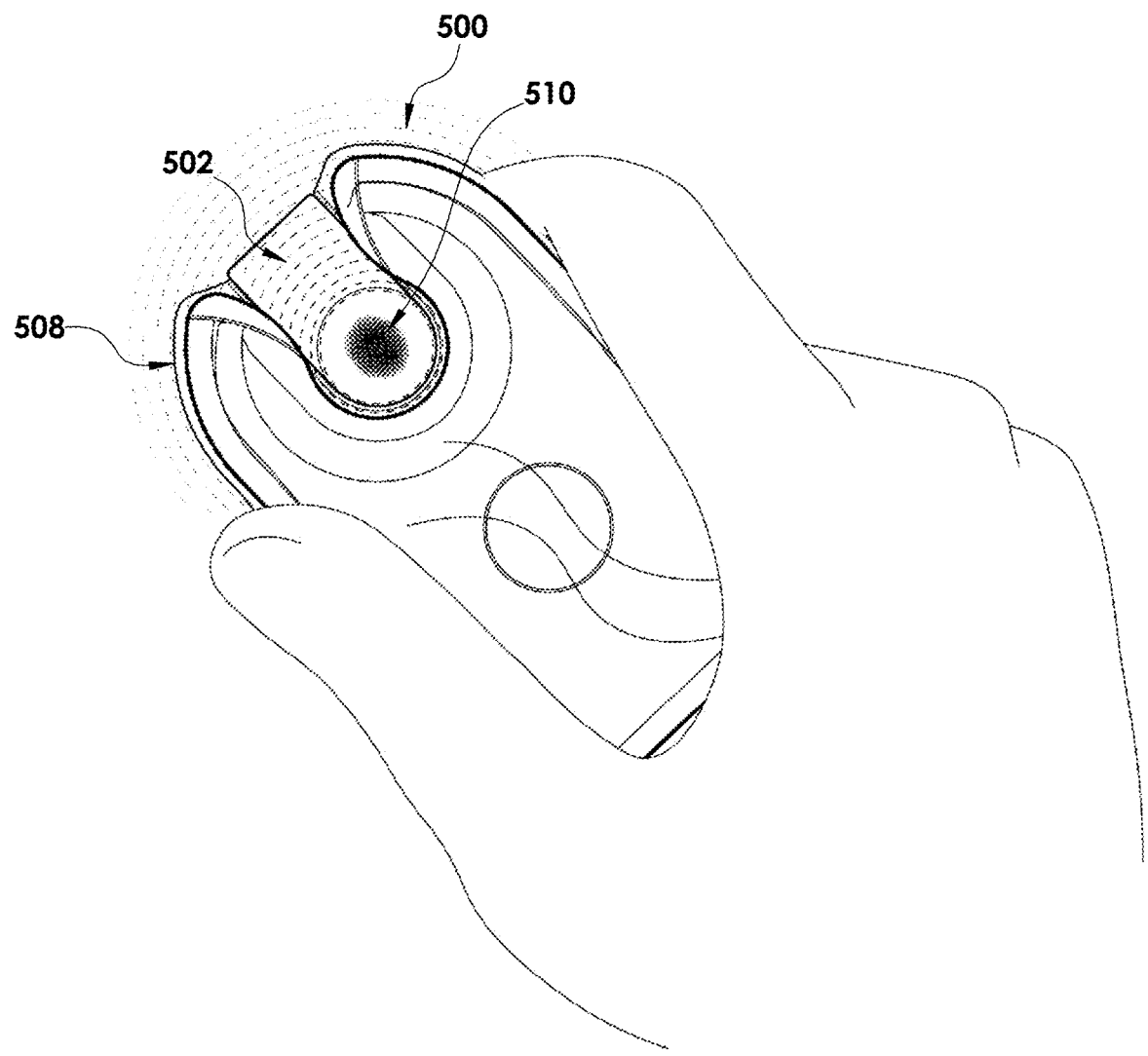
FIG. 51 is another view showing the illuminator during a bone marrow access apparatus locating procedure.
Figure 52:
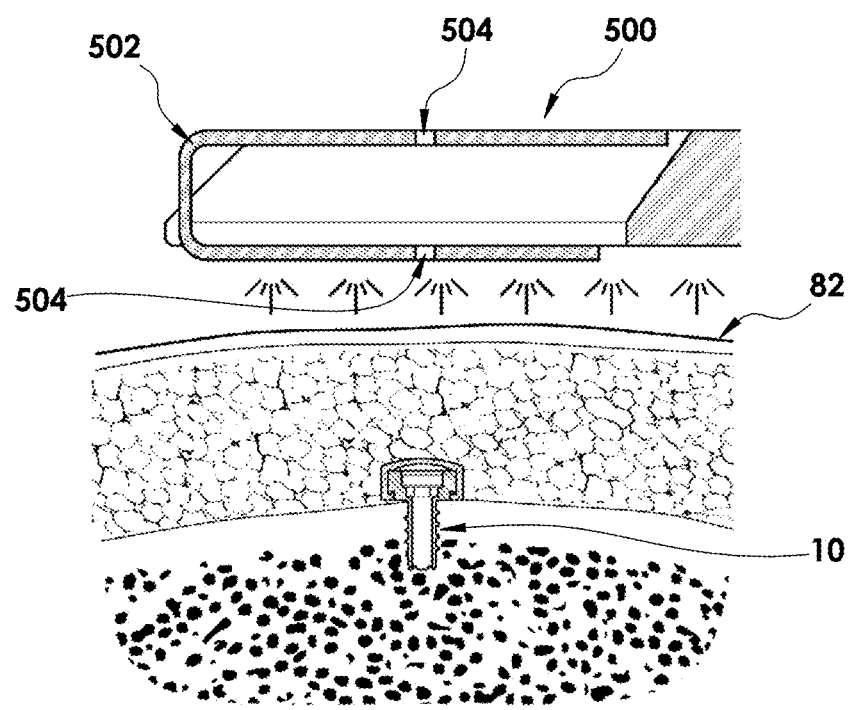
FIG. 52 is a cross-sectional view showing the illuminator during a bone marrow access apparatus locating procedure.
Figure 53:
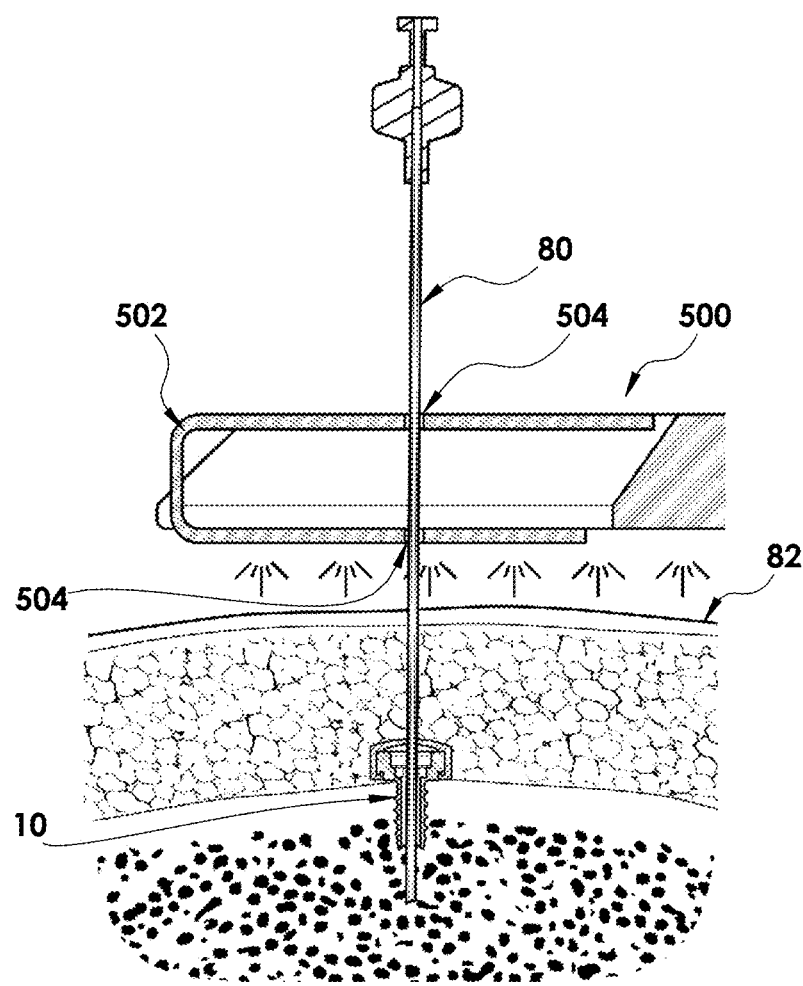
FIG. 53 is a cross-sectional view showing the illuminator during a bone marrow sampling procedure.

The physician moves the illuminator 500 to center the bone marrow access apparatus 10 in the aperture 506 and to align centering holes 504 in the clip 502 with the bone marrow access apparatus 10, by aligning the darker colored circle 510 with the centering holes 504 in the clip 502 (see FIG. 51). The holes 504 in the clip 502 ensure that the sampling needle 80 tracks to a center of the bone marrow access apparatus 10 in which the septum 52 (or valve 60) is located, as shown in FIG. 53.

Techniques for locating a bone marrow access apparatus are not limited to those described in the sixth and seventh embodiments. For example, a bone marrow access apparatus could be located using fluoroscopy, or using a magnetic or electromagnetic locator (similar in principle to a stud finder). Further techniques will be apparent to those of skill in the art.

Variations and combinations of the embodiments described above and illustrated in the drawings are considered to be within the scope of the invention, and thus the scope of the invention should be determined by the appended claims and their legal equivalents, rather than by the examples given.

In addition, apparatuses and methods disclosed in U.S. provisional patent application Ser. No. 62/062,105 filed Oct. 9, 2014, U.S. provisional patent application Ser. No. 62/404,551 filed Oct. 5, 2016, U.S. nonprovisional patent application Ser. No. 15/024,522 filed Mar. 24, 2016, now U.S. Pat. No. 9,770,425, U.S. nonprovisional patent application Ser. No. 15/486,870 filed Apr. 13, 2017, and U.S. nonprovisional patent application Ser. No. 15/486,886 filed Apr. 13, 2017 may be incorporated into and/or used with the inventions disclosed above, and all of these applications are incorporated by reference herein.

I claim:

1. A bone marrow access apparatus comprising:
a bone penetrating member; and
a cap;
wherein the bone penetrating member comprises:
   a tubular insertion portion;
   a head portion provided at a proximal end of the tubular insertion portion, a cross-sectional shape of the head portion being wider than a cross-sectional shape of the tubular insertion portion;
   a recess provided in the head portion; and
   an internal channel provided through the head portion and the tubular insertion portion;

wherein the cap accommodates the head portion of the bone penetrating member therein; and wherein the cap comprises:
- a lower wall which covers at least a part of a distal side of the head portion; and
- a projection which projects into the recess of the head portion.

2. The apparatus according to claim 1, wherein the recess extends around an entire circumference of the head portion; and
wherein projection extends around an entire circumference of the cap.

3. The apparatus according to claim 1, wherein the head portion of the bone penetrating member comprises a bottom surface at a distal end of the head portion, and a step portion which is peripherally outward of the bottom surface and is recessed upward with respect to the bottom surface;
wherein the recess is provided in the step portion;
wherein the lower wall of the cap is fitted in the step portion; and
wherein the projection projects from the lower wall into the recess.

4. The apparatus according to claim 3, wherein the step portion extends around an entire circumference of the head portion;
wherein recess extends around the entire circumference of the head portion; and
wherein projection extends around an entire circumference defined by the lower wall.

5. The apparatus according to claim 1, wherein the cap further comprises:
- an upper wall which covers a proximal side of the head portion of the bone penetrating member;
- a peripheral wall which covers a periphery of the head portion of the bone penetrating member.

6. The apparatus according to claim 5, wherein the upper wall of the cap comprises a self-healing septum.

7. The apparatus according to claim 5, wherein the upper wall of the cap comprises a valve.

8. The apparatus according to claim 1, wherein the cap further comprises a tactile feedback member comprising a projection which projects distally downward from the lower wall.

9. The apparatus according to claim 1, wherein the bone penetrating member is a separate component from the cap; and
wherein the bone penetrating member is assembled together with the cap to form the bone marrow access apparatus.

10. A bone marrow access apparatus comprising:
a bone penetrating member; and
a tactile feedback member which is coupled to the bone penetrating member;
wherein the bone penetrating member comprises:
a tubular insertion portion;
a head portion provided at a proximal end of the tubular insertion portion, a cross-sectional shape of the head portion being wider than a cross-sectional shape of the tubular insertion portion; and
an internal channel provided through the head portion and the tubular insertion portion;
wherein the tactile feedback member is provided at a distal side of the head portion of the bone penetrating member and projects distally downward with respect to the head portion of the bone penetrating member;
wherein the bone marrow access apparatus further comprises a cap which accommodates the head portion of the bone penetrating member therein;
wherein the cap comprises a lower wall which covers at least a part of a distal side of the head portion; and
wherein the tactile feedback member comprises a projection which projects distally downward from the lower wall.

11. The apparatus according to claim 10, wherein the projection extends continuously around an entire circumference of a bottom of the lower wall of the cap.

12. The apparatus according to claim 10, wherein the tactile feedback member comprises a plurality of projections which are spaced apart from each other around a circumference of a bottom of the lower wall of the cap.

13. The apparatus according to claim 10, wherein the projection of the tactile feedback member has a triangular cross-sectional shape.

14. The apparatus according to claim 10, wherein the head portion of the bone penetrating member comprises a bottom surface at a distal end of the head portion, and a step portion which is peripherally outward of the bottom surface and is recessed upward with respect to the bottom surface; and
wherein the lower wall of the cap is fitted in the step portion.

15. The apparatus according to claim 10, wherein the cap further comprises:
an upper wall which covers a proximal side of the head portion of the bone penetrating member; and
a peripheral wall which covers a periphery of the head portion of the bone penetrating member.

16. The apparatus according to claim 15, wherein the upper wall of the cap comprises a self-healing septum.

17. The apparatus according to claim 15, wherein the upper wall of the cap comprises a valve.

18. The apparatus according to claim 10, wherein the bone penetrating member is a separate component from the cap; and
wherein the bone penetrating member is assembled together with the cap to form the bone marrow access apparatus.

* * * * *